United States Patent
Bhattacharya et al.

(10) Patent No.: US 10,543,231 B2
(45) Date of Patent: Jan. 28, 2020

(54) METHODS AND MATERIALS FOR TREATING CANCER

(71) Applicant: Mayo Foundation for Medical Education and Research, Rochester, MN (US)

(72) Inventors: Santanu Bhattacharya, Ponte Vedra, FL (US); Debabrata Mukhopadhyay, Rochester, MN (US); Krishnendu Pal, Jacksonville, FL (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 15/981,656

(22) Filed: May 16, 2018

(65) Prior Publication Data

US 2018/0333432 A1    Nov. 22, 2018

Related U.S. Application Data

(60) Provisional application No. 62/508,887, filed on May 19, 2017.

(51) Int. Cl.
| | | |
|---|---|---|
| *A61K 33/24* | (2019.01) | |
| *A61K 47/64* | (2017.01) | |
| *A61P 35/00* | (2006.01) | |
| *A61K 31/7068* | (2006.01) | |
| *A61K 47/69* | (2017.01) | |
| *A61K 47/52* | (2017.01) | |

(52) U.S. Cl.
CPC .......... *A61K 33/24* (2013.01); *A61K 31/7068* (2013.01); *A61K 47/52* (2017.08); *A61K 47/64* (2017.08); *A61K 47/6923* (2017.08); *A61K 47/6929* (2017.08); *A61P 35/00* (2018.01)

(58) Field of Classification Search
CPC ....................................................... A61K 33/24
See application file for complete search history.

(56) References Cited

U.S. PATENT DOCUMENTS

| | | | |
|---|---|---|---|
| 5,134,107 A | 7/1992 | Narula | |
| 5,981,445 A | 11/1999 | Kirchnerova et al. | |
| 6,036,774 A | 3/2000 | Lieber et al. | |
| 6,274,552 B1 | 8/2001 | Tamarkin et al. | |
| 6,342,219 B1 | 1/2002 | Thorpe et al. | |
| 6,344,339 B1 | 2/2002 | Menrad et al. | |
| 6,448,077 B1 | 9/2002 | Rockwell et al. | |
| 6,528,051 B2 | 3/2003 | Tamarkin et al. | |
| 6,530,944 B2 | 3/2003 | West et al. | |
| 6,676,941 B2 | 1/2004 | Thorpe et al. | |
| 6,955,639 B2 | 10/2005 | Hainfeld et al. | |
| 7,060,802 B1 | 6/2006 | Trakht et al. | |
| 7,122,353 B2 | 10/2006 | Shen | |
| 9,012,723 B2 * | 4/2015 | Guo | C07K 14/415 800/285 |
| 2001/0005581 A1 | 6/2001 | Grant et al. | |
| 2001/0055581 A1 | 12/2001 | Tamarkin et al. | |
| 2002/0071843 A1 | 6/2002 | Li et al. | |
| 2003/0053983 A1 | 3/2003 | Tamarkin et al. | |
| 2003/0118657 A1 | 6/2003 | West et al. | |
| 2003/0147966 A1 | 8/2003 | Franzen et al. | |
| 2004/0022817 A1 | 2/2004 | Tardi et al. | |
| 2004/0038303 A1 | 2/2004 | Unger | |
| 2006/0022295 A1 | 2/2006 | Takafuji et al. | |
| 2006/0222595 A1 | 10/2006 | Mukherjee et al. | |
| 2006/0251726 A1 | 11/2006 | Lin et al. | |
| 2007/0099251 A1 * | 5/2007 | Zhang | G01N 33/574 435/7.23 |
| 2008/0227684 A1 | 9/2008 | Belmares et al. | |
| 2010/0009445 A1 | 1/2010 | Patra et al. | |
| 2012/0040915 A1 | 2/2012 | Mukhopadhyay et al. | |
| 2012/0288535 A1 | 11/2012 | Patra et al. | |
| 2013/0333061 A1 * | 12/2013 | Wu | C07K 14/415 800/260 |

FOREIGN PATENT DOCUMENTS

| | | | |
|---|---|---|---|
| WO | WO 02/32404 | 4/2002 | |
| WO | WO 04/83902 | 9/2004 | |
| WO | WO2008/143679 | * 11/2008 | ............... C12N 9/24 |

OTHER PUBLICATIONS

Allen et al., "Cellular delivery of MRI contrast agents," Chem. Biol., 11(3):301-307, Mar. 2004.
Awan et al., "5T4 interacts with TIP-2/GIPC, a PDZ protein, with implications for metastasis," Biochem. Biophys. Res. Commun., 290(3):1030-1036, Jan. 2002.
Bardeesy and DePinho, "Pancreatic cancer biology and genetics," Nat. Rev. Cancer, 2(12):897-909, Dec. 2002.
Berge et al., "Pharmaceutical salts," J. Pharm. Sci., 66:1-19, Jan. 1977.
Booth et al., "GIPC participates in G protein signaling downstream of insulin-like growth factor 1 receptor," J. Biol. Chem., 277(8):6719-6725, Feb. 2002.
Brekken et al., "Selective inhibition of vascular endothelial growth factor (VEGF) receptor 2 (KDR/Flk-1) activity by a monoclonal anti-VEGF antibody blocks tumor growth in mice," Cancer Res., 60(18):5117-5124, Sep. 2000.
Carmeliet and Jain, "Angiogenesis in cancer and other diseases," Nature, 407(6801):249-257, Sep. 2000.
Case et al., "The Amber biomolecular simulation programs," J. Chem. Chemistry, 26:1668, Dec. 2005.
Caulfield et al., "Examinations of tRNA Range of Motion Using Simulations of Cryo-EM Microscopy and X-Ray Data," J. Biophys., 2011:219515, Mar. 2011.
Caulfield et al., "Molecular dynamics simulations of human DNA methyltransferase 3B with selective inhibitor nanaomycin A," J. Struct. Biol., 176:185, Aug. 2011.

(Continued)

*Primary Examiner* — Amber D Steele
(74) *Attorney, Agent, or Firm* — Fish & Richardson P.C.

(57) ABSTRACT

This document provides methods and materials involved in treating cancer. For example, methods and materials involved in making and using particles (e.g., gold nanoparticles) containing a KTLLPTPYC amino acid sequence (SEQ ID NO:1) or a KTLLPTPYCC amino acid sequence (SEQ ID NO:2) to treat cancer (e.g., pancreatic cancer) are provided.

10 Claims, 10 Drawing Sheets
Specification includes a Sequence Listing.

(56) References Cited

OTHER PUBLICATIONS

Caulfield et al., "Motion of transfer RNA from the A/T state into the A-site using docking and simulations," Proteins, 80:2489, Jul. 2012.
Celano et al., "Cytotoxic effects of gemcitabine-loaded liposomes in human anaplastic thyroid carcinoma cells," BMC Cancer, 4:63, Sep. 2004.
Cheatham et al., "Molecular dynamics simulation of nucleic acids: successes, limitations, and promise," Biopolymers, 56:232, Dec. 2001.
Chen et al., "High-throughput screen for small molecule inhibitors of Mintl-PDZ domains," Assay Drug Dev. Technol., 5(6):769-783, Dec. 2007.
Copland et al., "Bioconjugated gold nanoparticles as a molecular based contrast agent: implications for imaging of deep tumors using optoacoustic tomography," Mol. Imaging Biol., 6(5):341-349, Sep.-Oct. 2004.
De Vries et al., "GIPC, a PDZ domain containing protein, interacts specifically with the C terminus of RGS-GAIP," Proc. Natl. Acad. Sci. U.S.A., 95(21):12340-12345, Oct. 1998.
El Mourabit et al., "The PDZ domain of TIP-2/GIPC interacts with the C-terminus of the integrin alpha5 and alpha6 subunits," Matrix Biol., 21(2):207-214, Mar. 2002.
Ferrara et al., "Molecular and biological properties of the vascular endothelial growth factor family of proteins," Endocr. Rev., 13:18-32, Feb. 1992.
Friesner et al., "Glide: a new approach for rapid, accurate docking and scoring. 1. Method and assessment of docking accuracy," J. Med. Chem., 47:1739, Mar. 2004.
Friesner et al., "Extra precision glide: docking and scoring incorporating a model of hydrophobic enclosure for protein-ligand complexes," J. Med. Chem., 49:6177, Oct. 2006.
Gao et al., "Synectin, syndecan-4 cytoplasmic domain binding PDZ protein, inhibits cell migration," J. Cell Physiol., 184(3):373-379, Sep. 2000.
Goldstein et al., "Response," J. Natl. Cancer Inst., 107(9), Aug. 2015.
Halgren et al., "Glide: a new approach for rapid, accurate docking and scoring. 2. Enrichment factors in database screening," J. Med. Chem., 47:1750, Mar. 2004.
Harder et al., "OPLS3: A Force Field Providing Broad Coverage of Drug-like Small Molecules and Proteins," J. Chem. Theory Comput., 12:281, Jan. 2016.
Hasson, "Myosin VI: two distinct roles in endocytosis," J. Cell Sci., 116(Pt 17):3453-3461, Sep. 2003.
Hirakawa et al., "GIPC binds to the human lutropin receptor (hLHR) through an unusual PDZ domain binding motif, and it regulates the sorting of the internalized human choriogonadotropin and the density of cell surface hLHR," J. Biol. Chem., 278(49):49348-49357, Dec. 2003.
Hu et al., "GIPC interacts with the β1-adrenergic receptor and regulates β1-adrenergic receptor mediated ERK activation.," J. Biol. Chem., 278(28):6295-26301, Jul. 2003.
Huang et al., "Synthesis and characterization of Eu: Y2O3 nanoparticles," Nanotechnology, 13(3):318-323, May 2002.
Humphrey et al., "VMD: visual molecular dynamics," J. Mol. Graph., 14:33, Feb. 1996.
Jeanneteau et al., "GIPC recruits GAIP (RGS19) to attenuate dopamine D2 receptor signaling," Mol. Biol. Cell, 15(11):4926-4937, Sep. 2004.
Jeanneteau et al., "Interactions of GIPC with dopamine D2, D3 but not D4 receptors define a novel mode of regulation of G protein-coupled receptors," Mol. Biol. Cell, 15(2):696-705, Feb. 2004.
Jorgensen et al., "Comparison of simple potential functions for simulating liquid water," J. Phys. Chem., 79:926, Apr. 1983.
Katoh, "GIPC gene family (Review)," Int. J. Mol. Med., 9(6):585-589, Jun. 2002.
Keck et al., "Vascular permeability factor, an endothelial cell mitogen related to PDGF," Science, 246(4935):1309-1312, Dec. 1989.
Kirikoshi and Katoh, "Expression of human GIPC1 in normal tissues, cancer cell lines, and primary tumors," Int. J. Mol. Med., 9(5):509-513, May 2002.
Krieger et al., "Increasing the precision of comparative models with YASARA NOVA—a self-parameterizing force field," Proteins, 47:393, May 2002.
Laskowski et al., "PROCHECK: a program to check the stereochemical quality of protein structures," J. Appl. Cryst., 26:283-291, Apr. 1993.
Leung et al., "Vascular endothelial growth factor is a secreted angiogenic mitogen," Science, 246(4935):1306-1309, Dec. 1989.
Ligensa et al., "A PDZ domain protein interacts with the C-terminal tail of the insulin-like growth factor-1 receptor but not with the insulin receptor," J. Biol. Chem., 276(36):33419-33427, Sep. 2001.
Liu et al., "PDZ domain protein GIPC interacts with the cytoplasmic tail of melanosomal membrane protein gp75 (tyrosinase-related protein-1)," J. Biol. Chem., 276(38):35768-35777, Sep. 2001.
Loo et al., "Nanoshell-enabled photonics-based imaging and therapy of cancer," Technol. Cancer Res. Treat., 3(1):33-40, Feb. 2004.
Lorber et al., "Flexible ligand docking using conformational ensembles," Protein Sci., 7:938, Apr. 1998.
Lou et al., "GIPC and GAIP form a complex with TrkA: a putative link between G protein and receptor tyrosine kinase pathways," Mol. Biol. Cell, 12(3):615-627, Mar. 2001.
Mangeney et al., "Synthesis and properties of water-soluble gold colloids covalently derivatized with neutral polymer monolayers," J. Am. Chem. Soc., 124(20):5811-5821, May 2000.
Mihailescu et al., "The effect of pH on amino acids binding to gold nanoparticles," J. Optoelectron. Adv. M., 9:756, Mar. 2007.
Moolhuizen et al., "Colloidal Gold Nanoparticles," Business Briefing: Pharmatech, 2004.
Muders et al., "Expression and regulatory role of GAIP-interacting protein GIPC in pancreatic adenocarcinoma," Cancer Res., 66(21):10264-10268, Nov. 2006.
Muders et al., "Targeting GIPC/synectin in pancreatic cancer inhibits tumor growth" Clin. Cancer Res., 15(12):4095-4103, Jun. 2009.
Muders et al.. "Is GIPC a new target for the treatment of pancreatic adenocarcinoma?" Proceedings of the Deutsche Gesellschafl !Or Pathologie [German Pathology Society] 91 st Conference, May 30-Jun. 2, 2007, pp. 286-293.
Ngo et al, "Computational complexity, protein structure prediction, and the Levinthal paradox," The protein folding problem and tertiary structure prediction. Birkhäuser Boston, pp. 491-495, 1994.
Okino et al., "Trans-tissue, sustained release of gemcitabine from photocured gelatin gel inhibits the growth of heterotopic human pancreatic tumor in nude mice," Clin. Cancer Res., 9:5786-5793, Nov. 2003.
Paciotti et al., "Colloidal gold: a novel nanoparticle vector for tumor directed drug delivery," Drug Deliv., 11(3): 169-183, May-Jun. 2004.
Papadatos-Pastos et al., "FOLFIRINOX—a new paradigm in the treatment of pancreatic cancer," Expert Rev. Anticancer Ther., 14:1115, Oct. 2014.
Patra et al., "Targeted delivery of gemcitabine to pancreatic adenocarcinoma using cetuximab as a targeting agent," Cancer Res., 68:1970, Mar. 2008.
Phillips et al., "Scalable Molecular Dynamics with NAMD," J. Comput. Chem., 26:1781-1802, May 2005.
Pol et al., "Synthesis of europium oxide nanorods by ultrasound irradiation," J. Phys. Chem. B, 106(38):9737-9743, Sep. 2002.
Prahst et al., "Neuropilin-1-VEGFR-2 complexing requires the PDZ-binding domain of neuropilin-1," J. Biol. Chem., 283:25110-25114, Sep. 2008.
Reblova et al., "Conformations of flanking bases in HIV-1 RNA DIS kissing complexes studied by molecular dynamics," Biophys. J., 93:3932, Dec. 2007.
Reblova et al., "Structure, dynamics, and elasticity of free 16s rRNA helix 44 studied by molecular dynamics simulations," Biopolymers, 82:504, Aug. 2006.
Rudchenko et al., "A human monoclonal autoantibody to breast cancer identifies the PDZ domain containing protein GIPC1 as a novel breast cancer-associated antigen," BMC. Cancer, 8:248, Aug. 2008.

(56) References Cited

OTHER PUBLICATIONS

Saro et al., "A thermodynamic ligand binding study of the third PDZ domain (PDZ3) from the mammalian neuronal protein PSD-95," Biochemistry, 46(21):6340-6352, May 2007.

Schenck et al., "The endosomal protein Appl1 mediates Akt substrate specificity and cell survival in vertebrate development," Cell, 133(3):486-497, May 2008.

Sehat et al., "Role of ubiquitination in IGF-1 receptor signaling and degradation," PLoS One, 2(4):e340, Apr. 2007.

Senger et al., "A highly conserved vascular permeability factor secreted by a variety of human and rodent tumor cell lines," Cancer Res., 46(11):5629-5632, Nov. 1986.

Shin et al., "Unexpected gain of function for the scaffolding protein plectin due to mislocalization in pancreatic cancer," Proc. Natl. Acad. Sci. USA, 110:19414, Nov. 2013.

Shivakumar et al., "Prediction of Absolute Solvation Free Energies using Molecular Dynamics Free Energy Perturbation and the OPLS Force Field," J. Chem. Theory Comput., 6:1509, May 2010.

Sykes et al., "Tailoring nanoparticle designs to target cancer based on tumor pathophysiology," Proc. Natl. Acad. Sci. USA, 113:E1142, Mar. 2016.

Tani and Mercurio, "PDZ interaction sites in integrin alpha subunits. T14853, TIP/GIPC binds to a type I recognition sequence in alpha 6A/alpha 5 and a novel sequence in alpha 6B," J. Biol. Chem., 276(39):36535-36542, Sep. 2001.

Varsano et al., "GIPC is recruited by APPL to peripheral TrkA endosomes and regulates TrkA trafficking and signaling," Mol. Cell Biol., 26(23):8942-8952, Dec. 2006.

Wang et al., "A PDZ protein regulates the distribution of the transmembrane semaphorin, M-SemF," J. Biol. Chem., 274(20):14137-14146, May 1999.

Wang et al., "C terminus of RGS-GAIP-interacting protein conveys neuropilin-1-mediated signaling during angiogenesis," FASEB J., 20(9):1513-5, Jul. 2006.

Wang et al., "Synthesis and characterization of lanthanide hydroxide single-crystal nanowires," Angew. Chem. Int. Ed. Engl., 41(24):4790-4793, Dec. 2002.

Wen et al., "Targeting PDZ domain proteins for treating NMDA receptor-mediated excitotoxicity," Curr. Top Med. Chem., 6(7):711-721, Apr. 2006.

Wu et al., "Kermit 2/XGIPC, an IGF1 receptor interacting protein, is required for IGF signaling in Xenopus eye development," Development, 133(18):3651-3660, Aug. 2006.

Yu et al., "Receptor-targeted nanocarriers for therapeutic delivery to cancer," Mol. Membr. Biol., 27:286, Oct. 2010.

Zeng et al., "KDR stimulates endothelial cell migration through heterotrimeric G protein Gq/11-mediated activation of a small GTPase RhoA," J. Biol. Chem., 277(48):46791-46798, Nov. 2002.

Zhang, "Gold Nanoparticles: Recent Advances in the Biomedical Applications," Cell Biochem. Biophys., 72:771, Jul. 2015.

Zhu et al, "Inhibition of tumor growth and metastasis by targeting tumor-associated angiogenesis with antagonists to the receptors of vascular endothelial growth factor," Invest. New Drugs, 17(3):195-212, Aug. 1999.

Zhu et al., "Nerve growth factor expression correlates with perineural invasion and pain in human pancreatic cancer," J. Clin. Oncol., 17(8):2419-2428, Aug. 1999.

\* cited by examiner

Untreated     GNP     GNP-Gem

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: polypeptides that bind to cancer cells

<400> SEQUENCE: 1

Lys Thr Leu Leu Pro Thr Pro Tyr Cys
1               5

<210> SEQ ID NO 2
<211> LENGTH: 10
<212> TYPE: PRT
<213> ORGANISM: Artificial Sequence
<220> FEATURE:
<223> OTHER INFORMATION: polypeptides that bind to cancer cells

<400> SEQUENCE: 2

Lys Thr Leu Leu Pro Thr Pro Tyr Cys Cys
1               5                   10

<210> SEQ ID NO 3
<211> LENGTH: 7
<212> TYPE: PRT
<213> ORGANISM: Artificial Sequence
<220> FEATURE:
<223> OTHER INFORMATION: polypeptides that bind to cancer cells
```

```
<400> SEQUENCE: 3

Lys Thr Leu Leu Pro Thr Pro
1               5

<210> SEQ ID NO 4
<211> LENGTH: 6
<212> TYPE: PRT
<213> ORGANISM: Artificial Sequence
<220> FEATURE:
<223> OTHER INFORMATION: polypeptides that bind to cancer cells

<400> SEQUENCE: 4

Val Tyr Met Ser Pro Phe
1               5

<210> SEQ ID NO 5
<211> LENGTH: 12
<212> TYPE: PRT
<213> ORGANISM: Artificial Sequence
<220> FEATURE:
<223> OTHER INFORMATION: polypeptides that bind to cancer cells

<400> SEQUENCE: 5

Tyr His Trp Tyr Gly Tyr Thr Pro Gln Asn Val Ile
1               5                   10

<210> SEQ ID NO 6
<211> LENGTH: 7
<212> TYPE: PRT
<213> ORGANISM: Artificial Sequence
<220> FEATURE:
<223> OTHER INFORMATION: polypeptides that bind to cancer cells

<400> SEQUENCE: 6

Met Gln Leu Pro Leu Ala Thr
1               5

<210> SEQ ID NO 7
<211> LENGTH: 7
<212> TYPE: PRT
<213> ORGANISM: Artificial Sequence
<220> FEATURE:
<223> OTHER INFORMATION: polypeptides that bind to cancer cells

<400> SEQUENCE: 7

Leu Ser Pro Pro Arg Tyr Pro
1               5

<210> SEQ ID NO 8
<211> LENGTH: 11
<212> TYPE: PRT
<213> ORGANISM: Artificial Sequence
<220> FEATURE:
<223> OTHER INFORMATION: polypeptides that bind to cancer cells

<400> SEQUENCE: 8

Lys Asn Gly Pro Trp Tyr Ala Tyr Thr Gly Arg
1               5                   10

<210> SEQ ID NO 9
<211> LENGTH: 8
<212> TYPE: PRT
<213> ORGANISM: Artificial Sequence
<220> FEATURE:
<223> OTHER INFORMATION: polypeptides that bind to cancer cells
```

```
<400> SEQUENCE: 9

Asp Pro Arg Ala Thr Pro Gly Ser
1               5

<210> SEQ ID NO 10
<211> LENGTH: 12
<212> TYPE: PRT
<213> ORGANISM: Artificial Sequence
<220> FEATURE:
<223> OTHER INFORMATION: polypeptides that bind to cancer cells

<400> SEQUENCE: 10

Val Pro Trp Met Glu Pro Ala Tyr Gln Arg Phe Leu
1               5                   10

<210> SEQ ID NO 11
<211> LENGTH: 12
<212> TYPE: PRT
<213> ORGANISM: Artificial Sequence
<220> FEATURE:
<223> OTHER INFORMATION: polypeptides that bind to cancer cells

<400> SEQUENCE: 11

His Leu Gln Leu Gln Pro Trp Tyr Pro Gln Ile Ser
1               5                   10

<210> SEQ ID NO 12
<211> LENGTH: 13
<212> TYPE: PRT
<213> ORGANISM: Artificial Sequence
<220> FEATURE:
<223> OTHER INFORMATION: polypeptides that bind to cancer cells

<400> SEQUENCE: 12

Cys Tyr Lys Asn Gly Pro Trp Tyr Ala Tyr Thr Gly Arg
1               5                   10
```

METHODS AND MATERIALS FOR TREATING CANCER

CROSS-REFERENCE TO RELATED APPLICATIONS

This application claims the benefit of U.S. Provisional Application Ser. No. 62/508,887, filed May 19, 2017. The disclosures of the prior applications are considered part of (and are incorporated by reference in) the disclosure of this application.

STATEMENT AS TO FEDERALLY SPONSORED RESEARCH

This invention was made with government support under CA078383 and CA150190 awarded by National Institutes of Health. The government has certain rights in the invention.

BACKGROUND

1. Technical Field

This document relates to methods and materials involved in treating cancer. For example, this document relates to methods and materials involved in using particles (e.g., gold nanoparticles) containing a KTLLPTYC amino acid sequence (SEQ ID NO:1) or a KTLLPTYCC amino acid sequence (SEQ ID NO:2) to treat cancer (e.g., pancreatic cancer).

2. Background Information

Pancreatic ductal adenocarcinoma (PDAC) is one of the deadliest human cancers with a five-year survival rate of 8% only. It is estimated to have 53,670 new cases and cause 43,090 deaths in 2017 in the United States, and the numbers have been steadily increasing over the years. The high mortality rate of PDAC patients is mainly attributed to an aggressive malignant phenotype, wide-spread metastasis and late-stage diagnosis. Current frontline treatments for PDAC such as FOLFIRINOX (a combination of leucovorin, 5-fluorouracil, irinotecan, and oxaliplatin) or Gemcitabine (Gem) with Abraxane provide modest survival benefits only (Goldstein et al., *J. Natl. Cancer Inst.,* 107 (2015); and Papadatos-Pastos et al., *Expert Rev. Anticancer Ther.,* 14:1115 (2014)). Moreover, a majority of these drugs are not tumor-selective, which ultimately results in systemic toxicity. Development of receptor-targeted nano drug delivery systems with the ability to specifically bind to receptors that are overexpressed in malignant cells is emerging as an attractive therapeutic alternative (Yu et al., *Mol. Membr. Biol.,* 27:286 (2010)). Among them, gold nanoparticles (GNPs) have attracted interest due to their ease of synthesis, chemical stability, excellent biocompatibility, and unique optical properties (Sykes et al., *Proc. Natl. Acad. Sci. USA,* 113:E1142 (2016); and Zhang, Cell *Biochem. Biophys.,* 72:771 (2015)).

SUMMARY

This document provides methods and materials involved in treating cancer. For example, this document relates to methods and materials involved in using particles (e.g., gold nanoparticles) containing a polypeptide having the amino acid sequence set forth in SEQ ID NO:1 or 2 to treat cancer (e.g., pancreatic cancer). This document also provides methods for making particles (e.g., gold nanoparticles) containing a polypeptide having the amino acid sequence set forth in SEQ ID NO:1 or 2.

As described herein, polypeptides including the amino acid sequence set forth in SEQ ID NO:1 or 2 can exhibit a reducing property that can be used to produce gold nanoparticles (GNPs) via an in situ reduction of gold (III) chloride in a one-pot, green synthesis. Polypeptides including the amino acid sequence set forth in SEQ ID NO:1 or 2 also can act as a template to generate highly monodispersed, spherical GNPs with a narrow size distribution and extended stability. The synthesized GNPs can be in situ surface modified with the polypeptides via the cysteine residue leaving the N-terminal KTLLPTP sequence (SEQ ID NO:3) free for targeting plectin-1, which is aberrantly expressed on the surface of pancreatic ductal adenocarcinoma (PDAC) cells. In some cases, the GNPs provided herein can be used to deliver therapeutic drugs such as Gemcitabine (Gem) specifically to PDAC tumors in a targeted manner. For example, GNPs conjugated to Gem can exhibit selective uptake in tumor tissues and selective antitumor activity.

In general, one aspect of this document features a composition comprising, or consisting essentially of, gold nanoparticles having a longest dimension of from about 5 nm to about 15 nm, wherein the gold nanoparticles comprise a polypeptide comprising a KTLLPTPYCC (SEQ ID NO:2) or KTLLPTPYC (SEQ ID NO:1) amino acid sequence. The longest dimension can be from about 6 nm to about 14 nm. The polypeptide can comprise the KTLLPTPYCC (SEQ ID NO:2) amino acid sequence. The polypeptide com can comprise the KTLLPTPYC (SEQ ID NO:1) amino acid sequence.

In another aspect, this document features a method for making gold nanoparticles having a longest dimension of from about 5 nm to about 15 nm. The gold nanoparticles comprise a polypeptide comprising an N-terminal CY or CCY amino acid sequence or a C-terminal YC or YCC amino acid sequence. The method comprises, or consists essentially of, (a) contacting gold material with the polypeptide to form a mixture; and (b) increasing the pH of the mixture, thereby forming the gold nanoparticles. The longest dimension can be from about 6 nm to about 14 nm. The polypeptide can comprise KTLLPTPYCC (SEQ ID NO:2). The polypeptide can comprise KTLLPTPYC (SEQ ID NO:1). The gold material can be gold (III) chloride trihydrate. The mixture can comprise a molar ratio of about 10:1 of the gold material to the polypeptide. The mixture can be stirred at 37° C. The method can comprise adding a base to the mixture to perform the increasing step. The base can be NaOH. The method can comprise increasing the pH to about 12.

In another aspect, this document features a method for treating a mammal having cancer. The method comprises administering, to the mammal, a composition comprising, or consisting essentially of, gold nanoparticles having a longest dimension of from about 5 nm to about 15 nm, wherein the gold nanoparticles comprise a polypeptide comprising a KTLLPTPYCC (SEQ ID NO:2) or KTLLPTPYC (SEQ ID NO:1) amino acid sequence. The longest dimension can be from about 6 nm to about 14 nm. The polypeptide can comprise the KTLLPTPYCC (SEQ ID NO:2) amino acid sequence. The polypeptide com can comprise the KTLLPTPYC (SEQ ID NO:1) amino acid sequence. The mammal can be a human. The cancer can be pancreatic cancer, liver cancer, lung cancer, breast cancer, hepatocellular carcinoma, prostate cancer, neuroblastoma, or cholangiocarcinoma. The composition can comprise a KTLLPTP (SEQ ID NO:3) amino acid sequence, and the cancer can be a pancreatic cancer.

In another aspect, this document features a method for treating a mammal having cancer. The method comprises administering, to the mammal, a composition comprising gold nanoparticles made using a method for making gold nanoparticles having a longest dimension of from about 5 nm to about 15 nm. The gold nanoparticles comprise a polypeptide comprising an N-terminal CY or CCY amino acid sequence or a C-terminal YC or YCC amino acid sequence. The method comprises, or consists essentially of, (a) contacting gold material with the polypeptide to form a mixture; and (b) increasing the pH of the mixture, thereby forming the gold nanoparticles. The longest dimension can be from about 6 nm to about 14 nm. The polypeptide can comprise KTLLPTPYCC (SEQ ID NO:2). The polypeptide can comprise KTLLPTPYC (SEQ ID NO:1). The gold material can be gold (III) chloride trihydrate. The mixture can comprise a molar ratio of about 10:1 of the gold material to the polypeptide. The mixture can be stirred at 37° C. The method can comprise adding a base to the mixture to perform the increasing step. The base can be NaOH. The method can comprise increasing the pH to about 12. The mammal can be a human. The cancer can be pancreatic cancer, liver cancer, lung cancer, breast cancer, hepatocellular carcinoma, prostate cancer, neuroblastoma, or cholangiocarcinoma. The composition can comprise a KTLLPTP (SEQ ID NO:3) amino acid sequence, and the cancer can be a pancreatic cancer.

In another aspect, this document features a method for treating a mammal having pancreatic cancer. The method comprises, or consist essentially of, administering, to the mammal, a composition comprising gold nanoparticles having a longest dimension of from about 5 nm to about 15 nm, wherein the gold nanoparticles comprise a polypeptide comprising a KTLLPTPYCC (SEQ ID NO:2) or KTLLPTPYC (SEQ ID NO:1) amino acid sequence, and wherein the gold nanoparticles enter cancer cells present within the mammal without entering more than 10 percent of non-cancerous pancreatic cells of the mammal. The mammal can be a human. The gold nanoparticles can enter less than 5 percent of the non-cancerous pancreatic cells.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
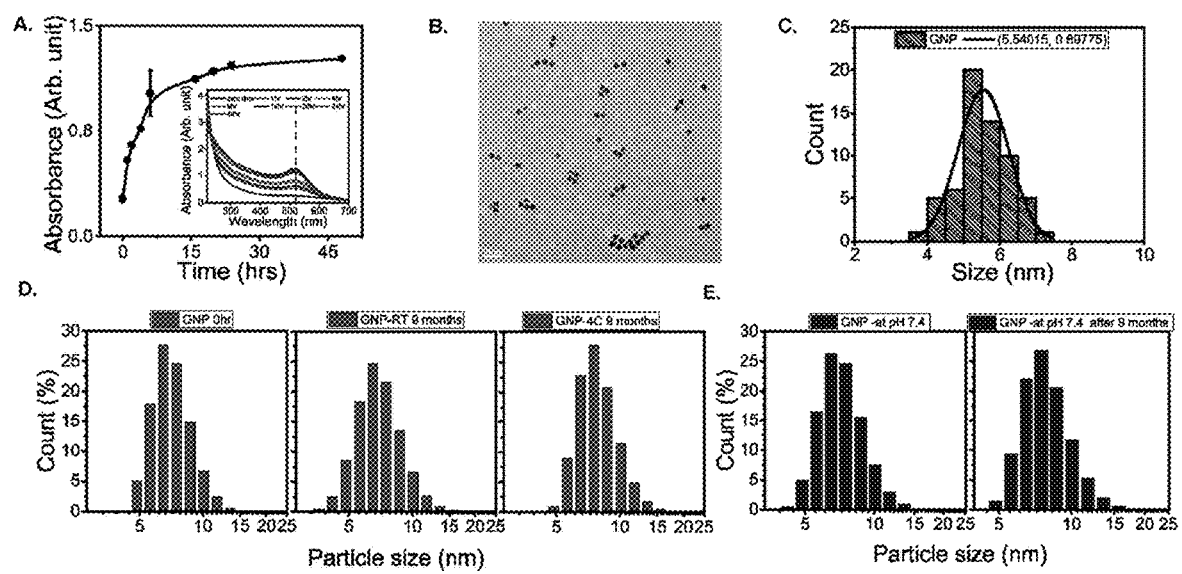
FIG. 1. Synthesis, characterization and stability of polypeptide-templated GNPs. A. Absorption intensity of the reaction solution at SPR peak as a function of time. (inset) UV-vis spectra of the reaction solution obtained at different time intervals. B. TEM image of the synthesized GNPs, scale bar=20 nm. C. GNP particle size distribution histogram obtained from TEM picture analysis. D. Long-term stability analysis of the synthesized GNPs after 9 months at room temperature (RT), 4° C. and E. at pH 7.4 by measuring respective hydrodynamic size distributions.

This document provides methods and materials involved in treating cancer. For example, this document provides methods and materials involved in using particles (e.g., gold nanoparticles) containing a polypeptide (e.g., a polypeptide having the amino acid sequence set forth in SEQ ID NO:1 or 2) to treat cancer (e.g., pancreatic cancer). This document also provides methods for making particles (e.g., gold nanoparticles) containing a polypeptide (e.g., a polypeptide having the amino acid sequence set forth in SEQ ID NO:1 or 2).

The methods and materials provided herein can be used to treat any appropriate type of cancer. For example, the methods and materials provided herein can be used to treat pancreatic cancer, liver cancer, lung cancer, breast cancer, hepatocellular carcinoma, prostate cancer, neuroblastoma, or cholangiocarcinoma. In some cases, the methods and materials provided herein can be used to treat cancer (e.g., pancreatic cancer) in any appropriate type of mammal including, without limitation, mice, rats, dogs, cats, horses, cows, pigs, monkeys, and humans.

In general, a particle (e.g., a nanoparticle) provided herein can be designed to include gold atoms and one or more polypeptides. As used herein, the term "gold nanoparticle" refers to particles having a longest linear dimension of from about 5 nm to about 15 nm. A gold nanoparticle provided herein can include any appropriate polypeptide. For example, a gold nanoparticle provided herein can include a polypeptide that binds to a particular molecule or target. In some cases, a gold nanoparticle provided herein can include a polypeptide that binds to cancer cells. For example, a gold nanoparticle provided herein can include a polypeptide having a KTLLPTP amino acid sequence (SEQ ID NO:3) that has the ability to bind a plectin-1 polypeptide expressed in the membrane of pancreatic cancer cells. Other examples of polypeptide sequences that can target a gold nanoparticle provided herein to a particular cancer cell are listed in Table 1. Additional polypeptide sequences that can target a gold nanoparticle provided herein to a particular cancer cell are listed in U.S. Pat. No. 7,122,353. See, e.g., Table 4 of U.S. Pat. No. 7,122,353, which is incorporated herein by reference, as noted above.

TABLE 1

| Sequence | Cancer | Target Molecule | SEQ ID NO: |
|---|---|---|---|
| KTLLPTP | Pancreatic cancer | Plectin-1 | 3 |
| VYMSPF | Pancreatic cancer, ovarian cancer and other type of cancer | FGFR-1 | 4 |
| YHWYGYTPQNVI | Pancreatic cancer, ovarian cancer and other type of cancer | EGFR | 5 |
| MQLPLAT | Pancreatic cancer, ovarian cancer and other type of cancer | FGFR1 | 6 |
| LSPPRYP | Pancreatic cancer, ovarian cancer and other type of cancer and other type of cancer | FGFR1 | 7 |
| KNGPWYAYTGR | B cell lymphoma | IgM λ receptor | 8 |
| DPRATPGS | Prostate cancer | LNCaP | 9 |
| VPWMEPAYQRFL | neuroblastoma | WAC-2 | 10 |
| HLQLQPWYPQIS | Breast cancer | MDA-MBA | 11 |

As described herein, a polypeptide to be incorporated into a gold nanoparticle can include an N-terminal CY or CCY amino acid sequence and/or a C-terminal YC or YCC amino acid sequence depending on the target sequence. In some cases, when an N-terminal targeting polypeptide is used to bind to a targeted protein, modification of the N terminal may interfere with targeting efficiency. In such cases, a C-terminal modification with YC or YCC can be used. In some cases, when a C-terminal targeting polypeptide is used to bind to the targeted protein, an N-terminal modification with CY or CCY can be used. In some cases, neither an N-terminal nor C-terminal portion is substantially involved in binding to a targeted protein. In such cases, terminal modifications with CY or CCY will not substantially reduce targeting efficiency of the targeting polypeptide, and the polypeptide can include an N-terminal CY or CCY amino acid sequence modification and/or a C-terminal YC or YCC amino acid sequence modification.

In some cases, any of the sequences set forth in Table 1 can include a C-terminal YC (e.g., KTLLPTP (SEQ ID NO:3) can be designed to be KTLLPTPYC (SEQ ID NO:1)) or an N-terminal CY (e.g., KNGPWYAYTGR (SEQ ID NO:8) can be designed to be CYKNGPWYAYTGR (SEQ ID NO:12).

In some cases, a gold nanoparticle provided herein can be designed to contain a single type of polypeptide or can be designed to contain two or more different polypeptides. For example, a gold nanoparticle provided herein can be designed to contain KTLLPTPYC (SEQ ID NO:1) polypeptides as the only type of polypeptide. As another example, a gold nanoparticle provided herein can be designed to contain KTLLPTPYC (SEQ ID NO:1) polypeptides and KTLLPT-PYCC (SEQ ID NO:2) polypeptides.

In some cases, gold nanoparticles provided herein can be designed to include one or more drugs (e.g., anti-cancer drugs such as chemotherapeutic agents). Examples of drugs that can be included as part of a gold nanoparticles provided herein include, without limitation, gemcitabine, leucovorin, 5-fluorouracil, irinotecan, oxaliplatin, doxirubicine, sorafinib, rogorafinib, CMET inhibitors, β-catenin inhibitors, and MET inhibitors. In some cases, a gold nanoparticle provided herein can be designed to include a single type of drug or can be designed to include two or more different drugs. For example, a gold nanoparticle provided herein can be designed to contain gemcitabine as the only drug. As another example, a gold nanoparticle provided herein can be designed to contain leucovorin, 5-fluorouracil, irinotecan, and oxaliplatin.

This document also provides methods for making gold nanoparticles. In some cases, a gold nanoparticle provided herein can be made by contacting gold material with a polypeptide to form a mixture. An example of a gold material that can be used to make a gold nanoparticle provided herein includes, without limitation, gold (III) chloride trihydrate. Any appropriate polypeptide can be used to make a gold nanoparticle provided herein. For example, a polypeptide having an amino acid sequence set forth in Table 1 can be used to make a gold nanoparticle provided herein. As described herein, such polypeptides can include an N-terminal CY or CCY amino acid sequence and/or a C-terminal YC or YCC amino acid sequence. Any appropriate ratio of gold material to polypeptide can be used. For example, the ratio of gold material to polypeptide can be from about 100:1 to about 1:1. In some cases, the ratio of gold material to polypeptide can be about 100:1, about 50:1, about 25:1, about 10:1, about 5:1, or about 1:1. Any appropriate temperature can be used to form the mixture of gold material and polypeptide. For example, the mixture can be formed at a temperature from about 27° C. to about 60° C., with or without optional stirring or mixing. In some cases, the mixture can be formed at about 37° C. with stirring. Any appropriate incubation time can be used to form the mixture of gold material and polypeptide. For example, the mixture can be formed using an incubation time from about 1 hour to about 24 hours. In some cases, the mixture can be formed using a 2-minute incubation time.

Once the mixture is formed and any incubation period is complete, a base can be added to the mixture to increase pH. Any appropriate base can be used including, without limitation, NaOH (e.g., 1M NaOH), KOH, or NH$_4$OH. In some cases, the pH of the mixture can be adjusted to reach a pH of from about 8 to about 13. For example, NaOH can be added to reach a pH of about 12.

In some cases, the process of mixing gold material and polypeptides together and adjusting the pH to from about 8 to about 13 can result in the formation of gold nanoparticles having containing polypeptides. Such gold nanoparticles can be contacted with one or more drugs to create gold nanoparticles containing both polypeptides and drugs. For example, gemcitabine can be immobilized on the surface of gold nanoparticles by passive adsorption such as via electrostatic interaction.

As described herein, a gold nanoparticle provided herein can be designed to include one or more targeting polypeptides to target cancer cells and one or more anti-cancer drugs. Such gold nanoparticles can be administered to a mammal to treat cancer. Any appropriate method can be used to administer a gold nanoparticle provided herein to a mammal. For example, a gold nanoparticle provided herein can be administered via injection (e.g., subcutaneous injection, intramuscular injection, intravenous injection, or intrathecal injection).

Before administering a gold nanoparticle provided herein to a mammal, the mammal can be assessed to determine whether or not the mammal has cancer (e.g., pancreatic cancer). Any appropriate method can be used to determine whether or not a mammal has cancer. For example, a mammal (e.g., human) can be identified as having cancer using standard diagnostic techniques. In some cases, a tissue biopsy can be collected and analyzed to determine whether or not a mammal has cancer.

After identifying a mammal as having cancer (e.g., pancreatic cancer), the mammal can be administered a composition containing gold nanoparticles provided herein. For example, a composition containing gold nanoparticles provided herein can be administered prior to or in lieu of surgical resection of a tumor. In some cases, a composition containing gold nanoparticles provided herein can be administered following resection of a tumor.

A composition containing gold nanoparticles provided herein can be administered to a mammal in any appropriate amount, at any appropriate frequency, and for any appropriate duration effective to achieve a desired outcome (e.g., to increase progression-free survival). In some cases, a composition containing gold nanoparticles provided herein can be administered to a mammal having cancer (e.g., pancreatic cancer) to reduce the progression rate of the cancer by 25, 50, 75, 90, or more percent. For example, the progression rate can be reduced such that no additional cancer progression is detected. Any appropriate method can be used to determine whether or not the progression rate of cancer is reduced. For example, the progression rate of cancer can be assessed by imaging tissue at different time points and determining the amount of cancer cells present. The amounts of cancer cells determined within tissue at different times can be compared to determine the progression rate. After treatment as described herein, the progression rate can be determined again over another time interval. In some cases, the stage of cancer after treatment can be determined and compared to the stage before treatment to determine whether or not the progression rate was reduced.

In some cases, a composition containing gold nanoparticles provided herein can be administered to a mammal having cancer (e.g., pancreatic cancer) under conditions where progression-free survival is increased (e.g., by 5, 10, 25, 50, 75, 99, or more percent) as compared to the median progression-free survival of corresponding mammals having untreated cancer (e.g., untreated pancreatic cancer). Progression-free survival can be measured over any appropriate length of time (e.g., one month, two months, three months, four months, five months, six months, or longer).

An effective amount of a composition containing gold nanoparticles provided herein can be any amount that reduces the progression rate of cancer (e.g., pancreatic cancer), increases the progression-free survival rate, or increases the median time to progression without producing significant toxicity to the mammal. Typically, an effective amount of a composition containing gold nanoparticles provided herein can be from about 10 mg/m$^2$ to about 200 mg/m$^2$ (e.g., from about 20 mg/m$^2$ to about 200 mg/m$^2$, from about 10 mg/m$^2$ to about 200 mg/m$^2$, from about 50 mg/m$^2$ to about 200 mg/m$^2$, from about 100 mg/m$^2$ to about 200 mg/m$^2$, from about 10 mg/m$^2$ to about 150 mg/m$^2$, from about 10 mg/m$^2$ to about 100 mg/m$^2$, from about 10 mg/m$^2$ to about 75 mg/m$^2$, or from about 70 mg/m$^2$ to about 75 mg/m²). If a particular mammal fails to respond to a particular amount, then the amount of a composition containing gold nanoparticles provided herein can be increased by, for example, two fold. After receiving this higher concentration, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the cancer (e.g., pancreatic cancer) may require an increase or decrease in the actual effective amount administered.

The frequency of administration can be any frequency that reduces the progression rate of cancer (e.g., pancreatic cancer), increases the progression-free survival rate, or increases the median time to progression without producing significant toxicity to the mammal. For example, the frequency of administration can be from about once a month to about three times a month, or from about twice a month to about six times a month, or from about once every two months to about three times every two months. The frequency of administration can remain constant or can be variable during the duration of treatment. A course of treatment with a composition containing gold nanoparticles provided herein can include rest periods. For example, a composition containing gold nanoparticles provided herein can be administered over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the cancer may require an increase or decrease in administration frequency.

An effective duration for administering a composition containing gold nanoparticles provided herein can be any duration that reduces the progression rate of cancer (e.g., pancreatic cancer), increases the progression-free survival rate, or increases the median time to progression without producing significant toxicity to the mammal. Thus, the effective duration can vary from several days to several weeks, months, or years. In general, the effective duration for the treatment of cancer can range in duration from several weeks to several months. In some cases, an effective duration can be for as long as an individual mammal is alive. Multiple factors can influence the actual effective duration used for a particular treatment. For example, an effective duration can vary with the frequency of administration, effective amount, use of multiple treatment agents, route of administration, and severity of the cancer (e.g., pancreatic cancer).

A composition containing gold nanoparticles provided herein can be in any appropriate form. For example, a composition containing gold nanoparticles provided herein can be in the form of a solution or powder with or without a diluent to make an injectable suspension. A composition containing gold nanoparticles provided herein also can contain additional ingredients including, without limitation, pharmaceutically acceptable vehicles. A pharmaceutically acceptable vehicle can be, for example, saline, water, lactic acid, mannitol, or combinations thereof.

After administering a composition containing gold nanoparticles provided herein to a mammal, the mammal can be monitored to determine whether or not the cancer (e.g., pancreatic cancer) was treated. For example, a mammal can be assessed after treatment to determine whether or not the progression rate of cancer was reduced (e.g., stopped). As described herein, any appropriate method can be used to assess progression and survival rates.

The invention will be further described in the following examples, which do not limit the scope of the invention described in the claims.

EXAMPLES

Example 1—One-pot Green Synthesis of Plectin-1-targeting Polypeptide-capped Gold Nanoparticles for Targeted Delivery of Gemcitabine in Pancreatic Cancer Reagents Gold (III) chloride trihydrate and sodium hydroxide were purchased from Sigma. The polypeptide KTLLPTPYC (SEQ ID NO:1) (>99% purity) was obtained from Mayo Clinic Proteomics Core Facility. Luciferin sodium salt was purchased from Gold Biotechnology. Antibody against Ki67 was purchased from Santa Cruz Biotechnology. Celltiter 96 Aqueous One Solution Cell Proliferation Assay was purchased from Promega. Gemcitabine was obtained as a pre-made formulation Gemzar from Mayo Clinic Pharmacy. Immunohistochemistry was performed using the IHC Select HRP/DAB kit from Millipore.

Cell Lines

Two pancreatic cancer cell lines, AsPC-1 and PANC-1, were used in this study. AsPC-1 (CRL-1682) and PANC-1 (CRL-1469) cells were from American Type Culture Collection (ATCC). AsPC-1 cell line was maintained in RPMI-1640 medium supplemented with 10% fetal bovine serum (FBS) and 1% penicillin-streptomycin. PANC-1 cells were maintained in Dulbecco's Modified Eagle's Medium supplemented with 10% FBS and 1% penicillin-streptomycin.

Synthesis and Characterization of Polypeptide-templated GNPs

A simple one-pot green synthetic route was utilized to synthesize polypeptide-templated GNPs. Briefly, Gold (III) Chloride Trihydrate and KTLLPTPYC (SEQ ID NO:1) polypeptide were dissolved in Milli-Q water in 10:1 molar ratio, and the mixture was stirred at 37° C. for 2minutes. Then, 1M NaOH was added dropwise to raise the pH of the solution to 12. The color of the reaction mixture instantly changed from yellow to dark brown. The reaction kinetics were monitored by taking out 100 µL of the reaction mixture at different time intervals, diluting it to 1mL with milli-Q water, and measuring the surface plasmon resonance peak (SPR) (typically ~520 nm) using a Shimadzu Spectrometer. Dilution was necessary as the high concentration of GNPs was not practical for measurements. Stirring was continued for 16 hours, and the color of the reaction mixture turned to a dark red color. The GNPs were isolated by ultracentifugation at 38000 RPM in a Beckmann Optima L-80 XP ultracentrifuge. The supernatant was discarded carefully without disturbing the loose pellet of GNPs at the bottom of the ultracentrifuge tubes. Finally, the volume was made up to the original reaction volume with Milli-Q water to get GNP stock solution. However, this stock solution was quite concentrated for physical characterizations, so a working stock was prepared by 10x dilution of the initial stock solution in Milli-Q water. The absorption spectra and hydrodynamic size of the synthesized GNPs were analyzed using Shimadzu Spectrometer and Malvern zetasizer, respectively. Particle size also was analyzed by Transmission Electron Microscopy (TEM) analysis. TEM studies were carried out using a JEOL-JEM 2100 instrument operating at 200kV. For a given sample, 200 µL of a given well-dispersed solution were placed on a carbon-coated 200-mesh copper grid, followed by drying the sample at ambient conditions.

Gemcitabine Conjugation to GNPs

For Gem conjugation, the GNP stock solution was tenfold diluted in Milli-Q water and mixed with increasing concentrations of Gem. The resulting mixtures were stirred for 16 hours followed by spectroscopic analysis and ultracentrifugation at 38000 rpm as described previously. The Gem content of the supernatant was determined by measuring the absorbance at 268 nm using Shimadzu Spectrometer and comparing with a standard curve prepared with known concentrations of Gem. The amount of Gem conjugated to GNPs was then calculated by subtracting the Gem content in the supernatant from the initial added amount.

Stability of GNPs and Gemcitabine-conjugated GNPs

The synthesized GNPs were kept in two different storage temperatures (room temperature and 4° C.) and at two different pH values (pH 7.4 and pH 5), and their stability were analyzed by measuring any change in hydrodynamic size distribution. For GNP-Gem, stability was tested only at room temperature.

Gemcitabine Release Profile 2 mL of GNP-Gem were placed in a dialysis tube (MWCO 3.5 kDa), and the dialysis tube was incubated in 40 mL of PBS in a 50 mL Centrifuge tube in a 37° C. rotary incubator. At different time intervals, 1 mL of the dialysate was withdrawn and replenished with 1 mL PBS. The amount of Gem released in the dialysate was determined by measuring the absorbance at 268 nm. The cumulative release was calculated and plotted against time to get a release curve for Gem. A similar experiment was performed in pH 5.

In Vitro Cell Viability Assay

About $5 \times 10^3$ cells were seeded in 96-well plates and treated with increasing doses of GNP, Gem, and GNP-Gem diluted in respective media. After a 1-hour incubation, cells were washed thrice with PBS, overlaid with 100 µL media containing serum and antibiotics, and incubated for another 72 hours. At the end of the incubation, cell viability was measured using Celltiter 96 Aqueous One Solution Cell Proliferation Assay (Promega) as per the manufacturer's protocol. Briefly, the media containing the treatments were aspirated from the plate and washed with PBS. Then, 100 µL media containing 20 µL One Solution reagent was added to each well. The plate was incubated at 37° C. for 30 minutes, and absorbance at 492 nm was measured using Spectramax i3x. Percentage viability was calculated as follows: Viability (%)=100* (ATreated−ABlank)/(AUntreated−ABlank).

In Vivo Tumor Growth Inhibition 6-8 weeks old male and female NOD-SCID-Gamma (NSG) mice were obtained from NCI and housed in the institutional animal facilities. About $1 \times 10^6$ luciferase-transfected PANC-1 cells suspended in 50 µL PBS were injected orthotopically into the pancreas of the mice. Tumors were allowed to grow for three weeks. Then, mice were randomized into four groups of ten (5 male mice and 5 female mice in each group), and 50 µg/mouse Gem, GNP-Gem with an equivalent Gem amount, or unconjugated GNPs were injected intraperitoneally three times a week for three weeks. Tumor growth was measured weekly using an IVIS bioimager after injecting Luciferin. After three weeks of treatment, mice were sacrificed, and tumors were harvested, measured with slide calipers, and weighed. Tumor volumes were calculated using the formula: V=0.5 X a X b², where 'a' is the longest tumor axis, and 'b' is the shortest tumor axis.

Histological Study

Tumors were harvested and fixed in neutral buffered 10% formalin at room temperature for 24 hours prior to embedding in paraffin and sectioning. Sections were deparaffinized and then subjected Hematoxylin and Eosin (H&E) and Ki67 staining according to manufacturer's instructions (DAB 150, Millipore). Stable diaminobenzidine was used as a chromogen substrate, and the sections were counterstained with a hematoxylin solution. Slides were digitized with Aperio AT2 slide scanner (Leica) and analyzed with imagescope software (Leica).

Statistical Analysis

Either OriginPro 2016 from Origin Lab Corporation or Microsoft Excel 2010 was used for data analysis. The independent-samples t-test was used to test the probability of significant differences between groups. Statistical significance was defined as $p<0.05$ (*), and statistical high significance was defined as $p<0.01$ (**). Error bars were given on the basis of calculated SD values where applicable.

Model Building

Figure 3:
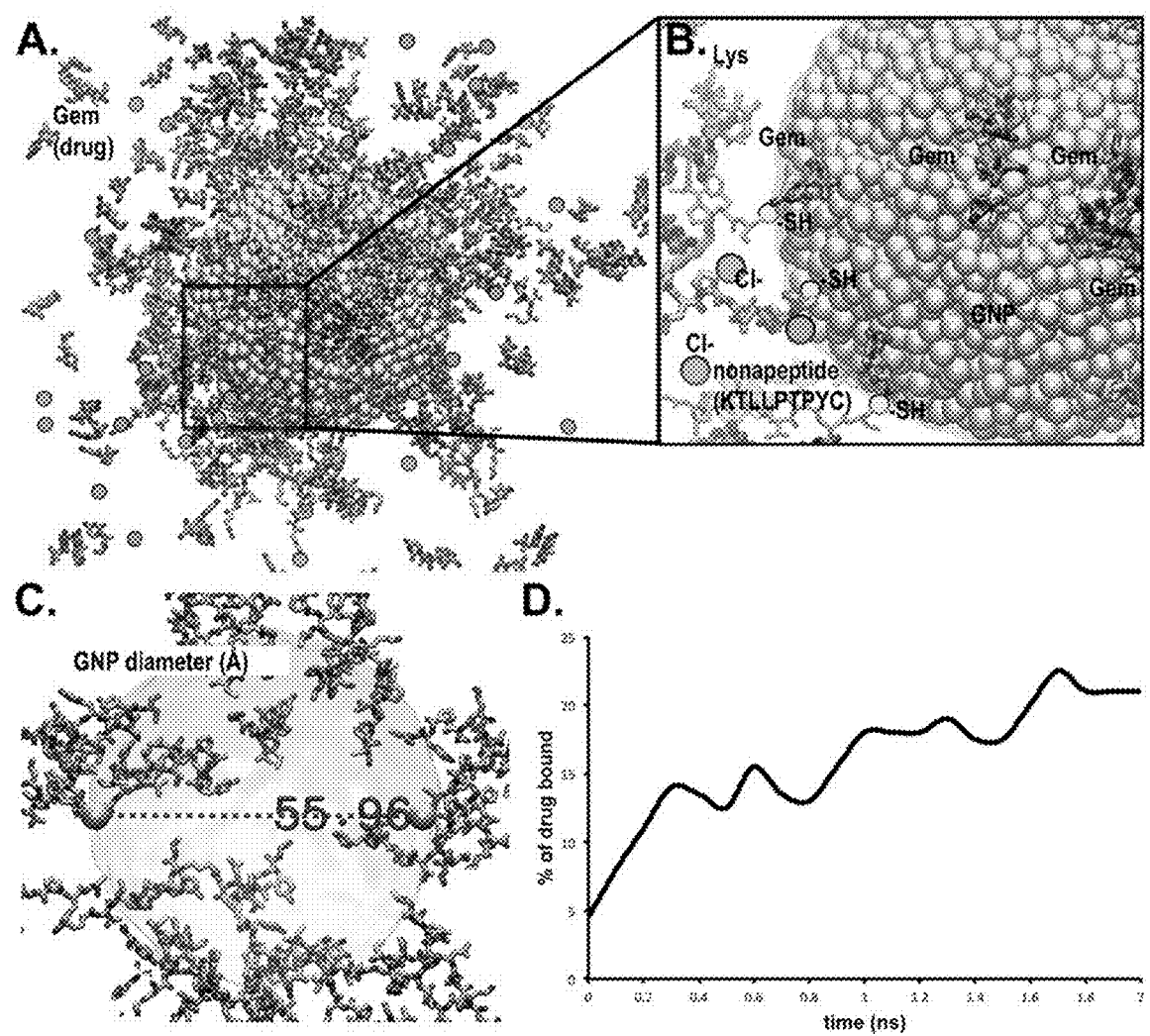
FIG. 3. Computational modeling of nonapeptide bound gold nanoparticle with drug capture. A model for a nonapeptide (KTLLPTPYC; SEQ ID NO:1) bound to 5.6 nm wide GNP via thiol-gold covalent linkages was generated with capture of Gemcitabine (Gem) drug for study of drug delivery transport mechanism. A. Entire nanoparticle consists of 4,896 Au atoms at the central core shown in yellow VdW spheres. Licorice stick peptides are displayed using conventional color for standard elements (carbon-gray, oxygen-red, nitrogen-blue, sulfur-yellow and hydrogen-white). Thicker stick rendering is shown for the Gemcitabine drug (highlighted ligand carbons colored red and fluorine in pink). Thiol (—SH)-to-gold connected cysteine atoms are shown in olive-yellow. Chlorine counter ions are shown in green spheres. B. Magnification of a representative area on GNP that reveals interaction of polypeptides and Gem with the GNP surface. N-terminal sequence of the polypeptides pointing away into solution is available for interacting with target proteins (plectin-1 in this case). C. Physical dimensions of the inner gold nanoparticle (~56 Å or 5.6 nm). D. Binding efficiency of GNP indicated by "% of drug bound", is increasing over time.

A gold nanoparticle (GNP) was built to a dimension of about 60 Å in diameter consisting of 4,896 Au atoms. The gold lattice was built within Visual Molecular Dynamics (VIVID) using a tcl-script and code to generate a gold lattice that could be subtracted using a spherical function from the origin (Humphrey et al., *J. Mol. Graph.*, 14:33 (1996)). This gold sphere was imported into Maestro for further molecular modeling. Nonapeptides were chosen with the sequence N-terminal-KTLLPTPYC-C-terminal to decorate the surface of the gold sphere via thiol linkages evenly spaced. The optimal number of peptides chosen was 53 with the N-terminal lysine facing into aqueous solution away from the GNP. The entire polypeptide fused GNP (53pep-GNP) consisted of 12,696 atoms. Additionally, 53 $Cl^-$ counter ions were added to the system to neutralize the $NH^{3+}$ charge from the terminal lysine. Further, 200 Gemcitabine drug molecules were introduced into the system, which consists of 5,799 atoms. Finally, physiological milieu of $Na^+$ and $Cl^-$ were added to a solvated box surrounding the 53pep-GNP using SPC water model. In total, the final simulation contained 205,500 atoms, which formed a cubic cell of 1,728 $nm^3$ (or $2.1 \times 10^6$ Å$^3$) (FIG. 3A-C).

Polypeptides were examined using Procheck and What-If (Krieger et al., *Proteins*, 47:393 (2002); and Laskowski et al., *J. Appl. Cryst.*, 26:283 (1993)). The side chains and rotamers were examined using refinement protocol and verified (Laskowski et al., *J. Appl. Cryst.*, 26:283 (1993)). The final system was subjected to energy optimization with PR conjugate gradient with an R-dependent dielectric for 100,000 steps with relaxing restraints. Each model was exported to the following formats: Maestro (MAE), VIVID (PDB). Model manipulation was done with Maestro (Macromodel, version 9.8, Schrödinger, LLC, New York, N.Y., 2010), or Visual Molecular Dynamics (VMD) (Humphrey et al., *J. Mol. Graph.*, 14:33 (1996)). The refinement modeling was built using Schrodinger Maestro and VIVID.

Nanoparticle Preparation

Following preparation of the base structure of the Au nanoparticle functionalized with peptide chains using VIVID and Maestro, the GNP model system was refined for molecular dynamics simulations by restraining the positions of Au atoms and SH— groups using the molecular builder tools in Schrödinger Materials Science Suite (Materials Science Suite, Version 2.2, Schrodinger, LLC, New York, N.Y., 2016). Detailed steps for the refinement of peptide-functionalized gold nanoparticle (GNP) representation in the presence of drug and water molecules can be summarized as follows: (i) all Au—Au bonds in GNP were removed to ease the force field (FF) setup stages, (ii) explicit representations of hydrogen atoms were added to the polypeptide chains, (iii) disordered system builder from Materials Science Suite was used to place 200 drug molecules near the functionalized GNP model, and finally (iv) water molecules with three-point model (SPC) was added inside the 3D periodic box that contains the GNP, peptide chains, and drug molecules to model the aqueous phase configuration. Energy minimization and the following dynamic simulation of the model system were performed by the molecular dynamics engine within Materials Science Suite, Desmond (Schrödinger Release 2016-4: Desmond Molecular Dynamics System, D. E. Shaw Research, New York, N.Y., 2016; Maestro-Desmond Interoperability Tools, Schrödinger, New York, N.Y., 2016). Structure-energy relationship of the molecular representations during the simulation was described by OPLS3 force field (Shivakumar et al., *J. Chem. Theory Comput.*, 6:1509 (2010); and Harder et al., *J. Chem. Theory Comput.*, 12:281 (2016)).

Equilibrating Simulations

Using the super-fast version of GPU-Desmond, a minimal equilibration was performed for 1.0 ns NVT simulation over the 250,000-atom system in just under 3 hours, and the nanoparticle stayed intact. Longer molecular dynamics simulations (MDS) were started using NVE/NPT ensembles for >400 ns.

Molecular Dynamics Simulation

The system was minimized with relaxed restraints using Steepest Descent and Conjugate Gradient PR and equilibrated in solvent with physiological salt conditions as described elsewhere (Caulfield et al., *Proteins*, 80:2489 (2012); Caulfield et al., *J. Struct. Biol.*, 176:185 (2011); and Caulfield et al., *J. Biophys.*, 2011:219515 (2011)). After equilibration was established, each system was allowed to run an additional MD production length of >10 nanoseconds. One purpose of MD for this study was conformational stability, refinement, and interaction calculations that may occur drug GNP interface. The protocol for refinement included the following steps: (1) Minimization with explicit water molecules and ions, (2) Energy minimization of the entire system, and (3) MDS for >10 ns to relax to the force field (OPLS3/Amber) (Harder et al., *J. Chem. Theory Comput.*, 12:281 (2016); and Case et al., *J. Chem. Chemistry*, 26:1668 (2005)). Following the refinement protocol, production simulations were completed to collect data.

Molecular Dynamics Protocol

OPLS3(Desmond)/Amber(NAMD2) force fields were used with the current release of NAnoscale Molecular Dynamics 2 engine (Case et al., *J. Chem. Chemistry*, 26:1668 (2005); and Phillips et al., *J. Comput. Chem.*, 26 (2005)). The system simulated, including hydrogens, consist of $2.5 \times 10^5$ atoms with solvation using SPC water and ions. In all cases, it was neutralized with counter-ions, and then a solvent was created with 150 mM $Na^+Cl^-$ to recreate physiological strength. SPC water molecules were added around the protein at a depth of 15-18 Å from the edge of the molecule depending upon the side (Jorgensen et al., *J. Chem. Physics*, 79:926 (1983); and Caulfield et al., *J. Biophys.*, 2011:219515 (2011)).

Simulations were carried out using the particle mesh Ewald technique with repeating boundary conditions with a 9 Å nonbonded cut-off, using SHAKE with a 2-fs timestep. Pre-equilibration was started with three stages of minimization with 10,000 steps of SD, PRCG, relaxing restraints, then followed by 1000 ps of heating under MD, with the atomic positions of nucleic and protein fixed. Then, two cycles of minimization (5000 steps each) and heating (1000 ps) were carried out with soft restraints of 10 and 5 kcal/(mol·Å2) applied to all backbone atoms and metals. Next, 5000-steps of minimization were performed with solute restraints reduced to 1 kcal/(mol·Å2). Following that, 400 ps of MDS were completed using relaxing restraints (1 kcal/(mol·Å2)) until all atoms are unrestrained, while the system was slowly heated from 1 to 310 K using velocity rescaling upon reaching the desired 310K during this equilibration phase. Additionally, NPT equilibration based MD was used with velocity rescaling for >10 ns. Finally, production runs of MD were carried out with constant pressure boundary conditions (relaxation time of 1.0 ps). A constant temperature of 310 K was maintained using the Berendsen weak-coupling algorithm with a time constant of 1.0 ps. SHAKE constraints were applied to all hydrogens to eliminate X-H vibrations, which yielded a longer simulation time step (2 fs). The methods for equilibration and production run protocols are described elsewhere (Caulfield et al., *Proteins*, 80:2489 (2012); Caulfield et al., *J. Struct. Biol.*, 176:185 (2011); Reblova et al., *Biopolymers*, 82:504 (2006); and Reblova et al., *Biophys. J.*, 93:3932 (2007)). Translational and rotational center-of-mass motions were initially removed. Periodically, simulations were interrupted to have the center-of-mass removed again by a subtraction of velocities to account for the "flying ice-cube" effect (Cheatham et al., *Biopolymers*, 56:232 (2001)). Following the simulation, the individual frames were superposed back to the origin, to remove rotation and translation effects.

Results

GNPs were developed in a one-pot green synthetic procedure by employing a KTLLPTPYC (SEQ ID NO:1) polypeptide that reduces Gold (III) Chloride Trihydrate and simultaneously acts as a template for controlling the growth of nascent gold nanoparticles. This allowed for the generation of highly stable monodispersed spherical GNPs with a narrow size distribution that were in situ surface-modified with plectin-1-targeting polypeptides (PTP). Physical characterizations were performed, and the stability and gemcitabine conjugation efficiency of the GNPs were analyzed. In addition, the gemcitabine release kinetics from the gemcitabine-conjugated GNPs (GNP-Gem) were evaluated as were the in vitro and in vivo therapeutic potential of GNP-Gem in two established pancreatic cancer cell lines and a PANC-1xenograft model, respectively.

The polypeptide-capped GNPs were produced in a simple one-pot green synthetic route. Here, a KTLLPTPYC (SEQ ID NO:1) polypeptide was used both as an in situ reducing agent and a template to prepare PTP-grafted GNPs from gold (III) chloride trihydrate.

When using the polypeptide with a C-terminal -YC sequence, only NaOH was used to increase the reducing potential of the tyrosine moiety to prepare GNPs in a single step. Different molar ratios of the reagents and various reaction conditions were tested. An effective ratio was found to be a 1:0.1:10 molar ratio of gold (III) chloride:polypeptide:NaOH, and an effective reaction temperature was 37° C. The reaction kinetics revealed that the reaction was almost complete within 16 hours as evident from the characteristic surface plasmon resonance (SPR) peak of synthesized gold nanoparticles at ~520 nm (FIG. 1A and inset). Further reaction did not significantly increase the SPR peak, and the monodispersity of the particles started to decline with time. Therefore, 16 hours was selected as a standard reaction time for the experiments.

The synthesized GNPs were purified from the reaction mixture by ultracentrifugation at 38000 RPM at 4° C. for one hour. The pellet was resuspended in Milli-Q water up to the original reaction volume to obtain a GNP stock solution. The stock solution, however, was quite concentrated for practical measurements, so all the experiments were performed using a working stock prepared by 10× dilution of the initial stock solution in Milli-Q water.

The transmission electron microscopy (TEM) images of the synthesized GNPs revealed uniform distribution of monodispersed spherical nanoparticles (FIG. 1B; scale bar 20 nm). The particle size distribution obtained from FIG. 1B revealed a narrow distribution of particles with diameter 5.5±0.6 nm (FIG. 1C). The hydrodynamic size distribution of the particles was also analyzed by dynamic light scattering (DLS) in a Malvern zetasizer, where the histogram analysis revealed a uniform distribution of particles centered around 6.5 nm (FIG. 1D, left panel). The stability of the GNPs at two different storage conditions (room temperature and 4° C.) was tested by measuring their hydrodynamic size distributions after 9 months of storage. The GNPs exhibited excellent long-term stability without significant aggregation in both storage temperatures for 9 months as evident from their hydrodynamic size distributions (FIG. 1D, middle and right panels). At physiological pH of 7.4, these GNPs exhibited similar outstanding stability with no substantial change in hydrodynamic size distributions over a period of 9 months (FIG. 1E). At pH 5, however, GNPs tended to aggregate more rapidly (data not shown). This was not at all surprising since at such acidic conditions there can be significant influence on GNP's surface charge which can result in aggregation (Mihailescu et al., *J. Optoelectron. Adv. M.*, 9:756 (2007)).

Figure 2:
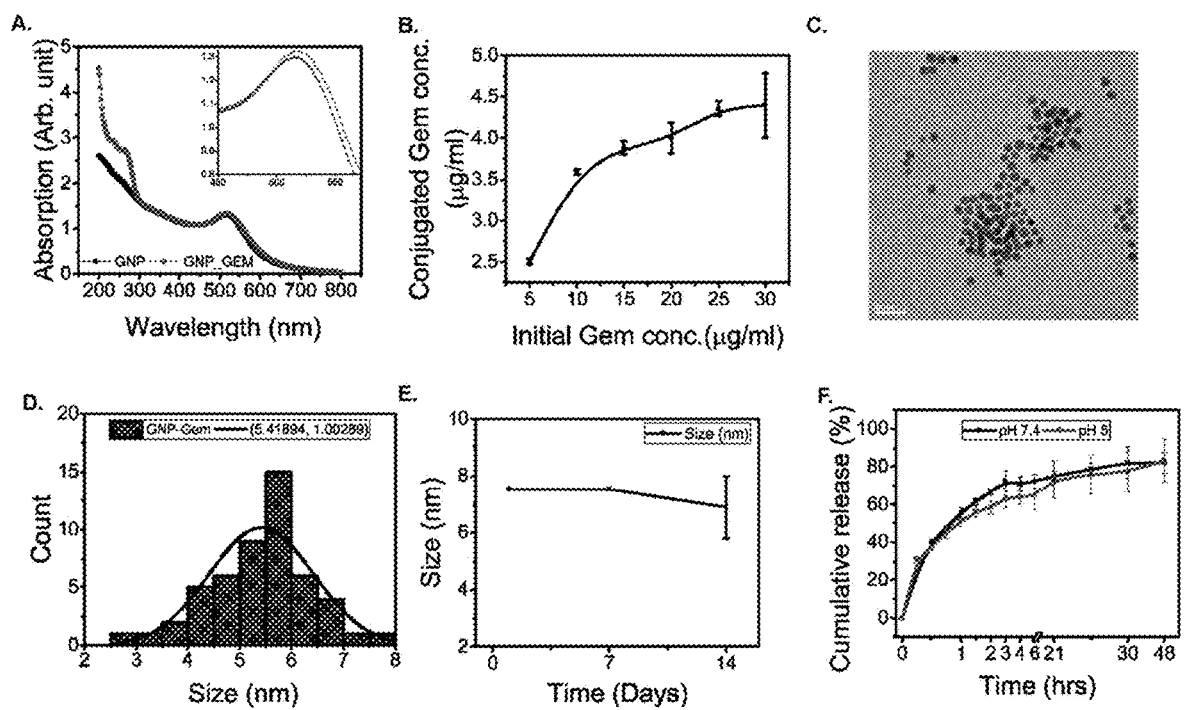
FIG. 2. Fabrication, characterization, and stability of GNP-Gem. A. UV-vis spectra of GNP (Black) and GNP-Gem (Red). (inset) magnified portion of the spectra to highlight the red shift of the SPR peak upon gemcitabine conjugation. B. Saturation curve for gemcitabine conjugation to the GNPs. C. TEM image of the GNP-Gem, scale bar=20 nm. D. GNP-Gem particle size distribution histogram obtained from TEM picture analysis. E. Stability analysis of the GNP-Gem at room temperature by monitoring hydrodynamic diameter for 14 days. F. In vitro cumulative gemcitabine release curve for GNP-Gem at 37° C. in two different pH environments. Black and red lines represent pH 7.4 and pH 5 respectively.

Since an objective of this work was to evaluate the efficacy of these GNPs as delivery vehicles, the conjugation efficiency of Gem to the GNPs was analyzed. For this purpose, increasing concentrations of Gem were added to 1 mL working stock of GNPs prepared by 10× dilution of the initial stock solution in Milli-Q water, and the mixture was stirred for 16 hours. Conjugation of Gem was confirmed by a slight red shift of the SPR peak (FIG. 2A and inset) in agreement with reports described elsewhere (Patra et al., *Cancer Res.*, 68:1970 (2008)). Ultracentrifugation at 38000 rpm for 1 hour allowed the Gem-conjugated GNPs (GNP-Gem) to be separated as a loose pellet from the reaction mixture, and the Gem content of the pellet was calculated by subtracting the Gem content of the supernatant from the amount of Gem initially added. The Gem content in the supernatants was determined by measuring the absorbance at 268 nm and comparing it with a standard curve prepared against known concentrations of Gem as described elsewhere (Celano et al., *BMC Cancer*, 4:63 (2004)). Finally, the Gem content of the pelleted GNPs was plotted against the initial added amount to get a saturation curve (FIG. 2B). The GNPs appeared to be saturated at a Gem concentration of 25 µg/mL, and about 4.25 µg/mL of Gem was found to be conjugated in the pellet. Therefore, the conjugation efficiency was about 17 percent.

Figure 7:
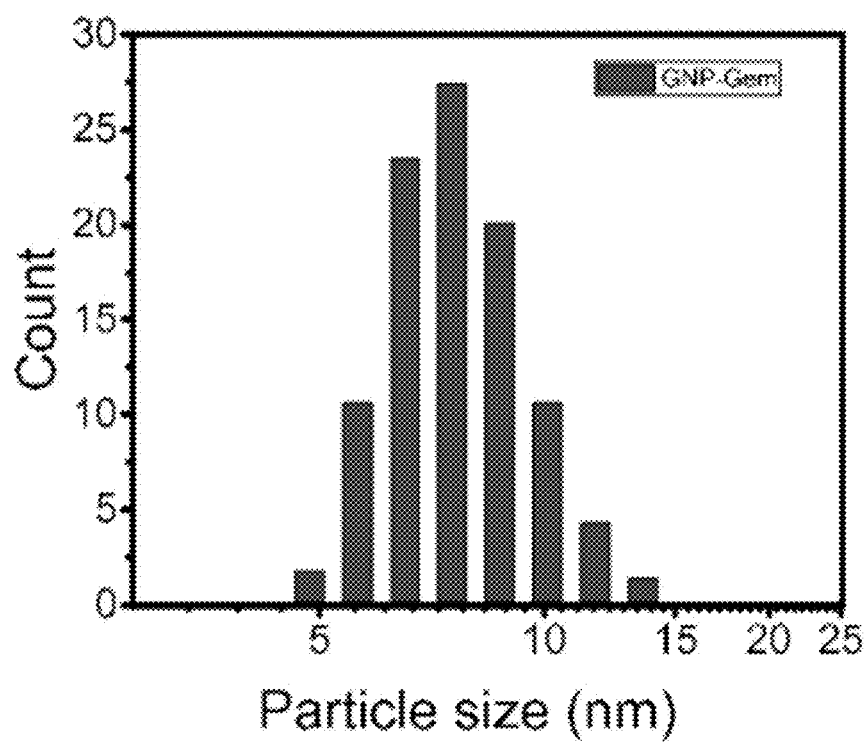
FIG. 7. Hydrodynamic size distribution of GNP-Gem.
Figure 8:
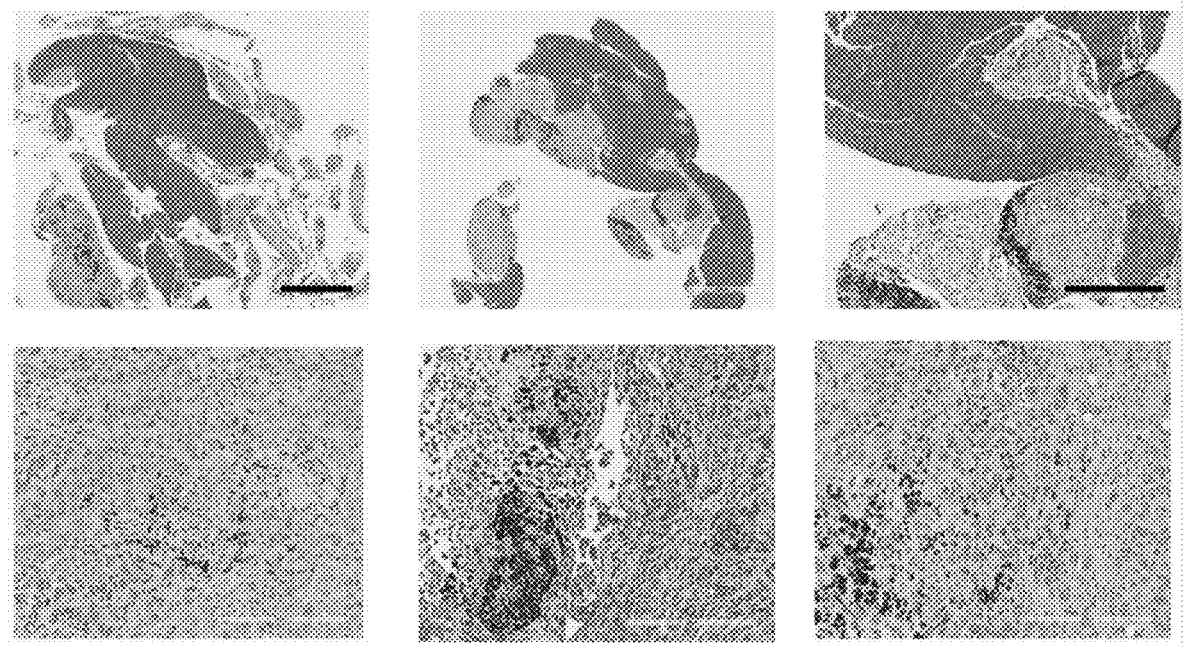
FIG. 8. Immunohistochemical analysis. A. Upper Panel, H&E staining of a tissue section from GNP-Gem treated group showing tumor-specific uptake of GNP-Gem without touching adjacent normal pancreas tissue. Scale bar=800 µm. Lower Panel, Higher magnification showing accumulation of GNPs in tumor tissue.

GNP-Gem also was analyzed for its size distribution and stability. The TEM image revealed a uniform population of the particles (FIG. 2C). The histogram analysis revealed a narrow distribution of particles with a diameter of 5.4±1 nm (FIG. 2D). The hydrodynamic size distribution revealed a uniform distribution of particles as well centered around 7.5 nm (FIG. 7). All these data pertaining to the increase in particle size suggested conjugation with Gem. The stability of the GNP-Gem also was analyzed by monitoring the hydrodynamic size at regular intervals at room temperature. No significant changes were observed from initial measurements up to 7 days, indicating that the stable dispersion of GNPs was still maintained after conjugation of Gem (FIG. 2E). The particles, however, did exhibit a decrease in size at day 14, presumably due to slow release of Gem from GNP-Gem.

Stability of the drug-loaded nanoparticles is needed for reaching the target. Once it reached the target, however, it also needs to release the drug efficiently. So, the release kinetics at physiological conditions were evaluated before moving forward with efficacy studies. To this end, the Gem release profile from the Gem-conjugated GNPs at 37° C. in two different pH environments (pH 7.4 and pH 5) was analyzed. No significant difference in release kinetics in different pH environments was found, suggesting that the release of Gem was not pH dependent. In both cases, there was an initial burst release followed by a sustained release (FIG. 2F). About 60-70% of the drug was released within the initial 4-hour period followed by a sustained release of 15-20% over a period of 48 hours. These results demonstrated efficient drug release from the Gem-conjugated GNPs at physiological conditions.

Modeling Gem using statistical mechanics approaches and molecular mechanics with simulations gives improved results over a docking only approach (Lorber et al., *Protein Sci.*, 7:938(1998)). Small simulation was completed to study Gem affinity for the gold nanoparticle (GNP) with the 53 bound nonapeptides with sequence KTLLPTPYC (SEQ ID NO:1) (PTP) (FIG. 3A-B). The water box size consisted of over 2 million cubic Å (or 1728 nm3); giving the system over 205,000 atoms within the box, and the box had dimensions of about 128 Å per edge (X, Y, Z). The 53 polypeptides found to be attached to the gold nanoparticle consisted of 12,696 atoms by its C terminal cysteine leaving N-terminal of PTP available to act as targeting agents. The gold nanoparticle had an inner diameter of 55.96 Å or about 5.6 nm (FIG. 3C), which was a close match with the TEM observations. The particle was free to tumble and migrate during simulation; however, periodic boundary conditions with Particle-Mesh Ewald were utilized to ensure accuracy.

When examining the particle up close (FIG. 3B), the bulk of the captured drug had interacted via the peptides and some Van der Waals (VdW) contacts with the gold nanoparticle, but without the polypeptides bound to the gold nanoparticle, the drugs did not aggregate as strongly. The Gem concentration increased from under 6% to nearly 25% over the course of the initial NPT simulations (FIG. 3D), which was strongly in agreement with the experimental observations. This corresponded to having over 42 of the 200 drug molecules in the water box becoming captured by the nanoparticle. Simulations for the entire complex were obtained.

Free energy (ΔGassociation) of binding were implemented within the software algorithm considering factors such as: lipophilicity, displacement of water, hydrogen bonding and electrostatic interactions, and metal ion/ligand interactions as favorable interactions; while the desolvation of polar or charged groups, restriction of motion, and the entropic cost of binding adversely affected free energy (Lorber et al., *Protein Sci.*, 7:938 (1998); Friesner et al., *J. Med. Chem.*, 47:1739 (2004); Friesner et al., *J. Med. Chem.*, 49:6177 (2006); and Halgren et al., *J. Med. Chem.*, 47:1750 (2004)). These energetic measurements can be used to determine optimal gold nanoparticle complexes for future drug delivery systems by measuring the total bound drug number and its combined free energy associated over time. This can then be correlated to the experimental value for conjugated Gem found in concentration directly from experiment and can act as a useful filter prior to experiment to guide the testing in a cost saving hypothesis generation.

Figure 4:
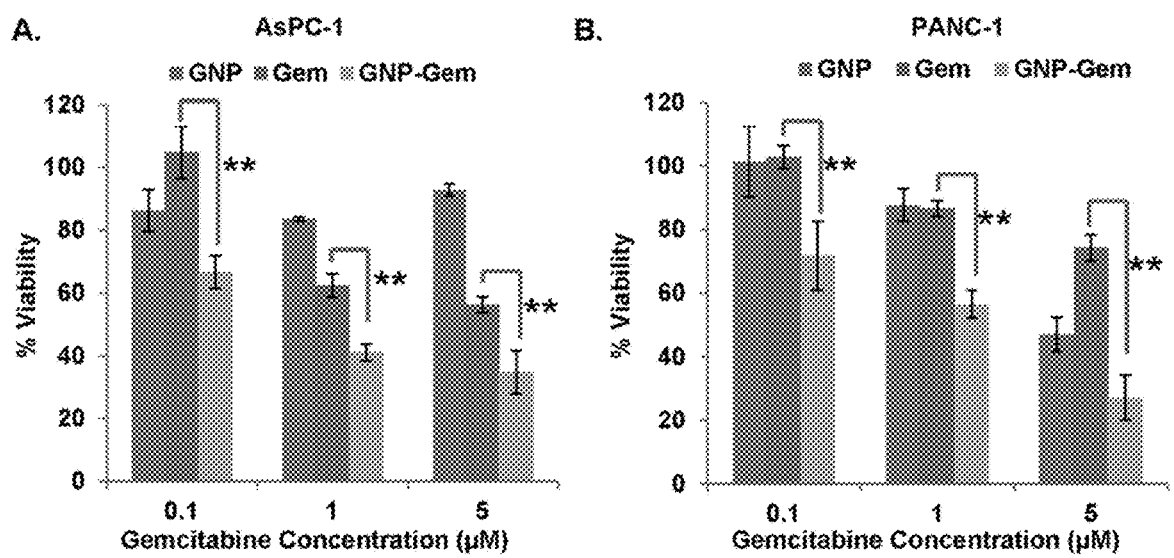
FIG. 4. In vitro therapeutic efficacy of GNP-Gem. In vitro cell viability as measured by MTS assay in A. AsPC-1 and B. PANC-1 cells after treating with increasing concentrations of Gem (blue), GNP (red), and GNP-Gem (green), respectively. ** denotes $p<0.01$.

Before analyzing the in vivo efficacy of GNP-Gem, the following was performed to test whether they were indeed demonstrating a superior inhibitory effect in pancreatic cancer cell viability. To this end, two commercially available pancreatic cancer cell lines were selected (AsPC-1 and PANC-1, obtained from ATCC). The cells were treated with increasing doses of GNP, Gem, and GNP-Gem for 1 hour. After 1 hour, cells were washed three times with PBS to remove the treatments completely in order to reduce any non-specific effect, and fresh media was added to the cells. The cell viability measurement was performed by MTS assay after 72 hours (FIG. 4A-B). Among the treatment groups, GNP-Gem exhibited the maximum inhibitory effect in both cell lines. Interestingly, GNPs also exhibited a significant effect in PANC-1 cells especially at 5 $\mu$M, but no dose dependent effect was observed in AsPC-1 cells (FIG. 4A). Similarly, Gem exhibited a dose dependent effect in AsPC-1 cells, but not in PANC-1 cells (FIG. 4B). The effects exhibited by GNPs may be partly due to the binding of the polypeptide on the GNP surface to plectin-1 since plectin-1 was shown to have important functions in pancreatic cancer pathogenesis (Shin et al., *Proc. Natl. Acad. Sci. USA*, 110:19414 (2013)). Nonetheless, the results obtained from these experiments demonstrated that GNP-Gem exerted a superior inhibitory effect on pancreatic cancer cell viability compared to GNP or Gem alone.

Since gemcitabine-conjugated GNPs demonstrated enhanced anti-proliferative activity in PDAC cells in vitro, the following was performed to evaluate the in vivo therapeutic potential of the same in a PANC-1 xenograft model. PANC-1 was selected for an in vivo experiment because it exhibited higher Gem resistance in vitro compared to AsPC-1, and the test involved determining whether conjugation of Gem to GNPs can increase the therapeutic efficacy.

Figure 5:
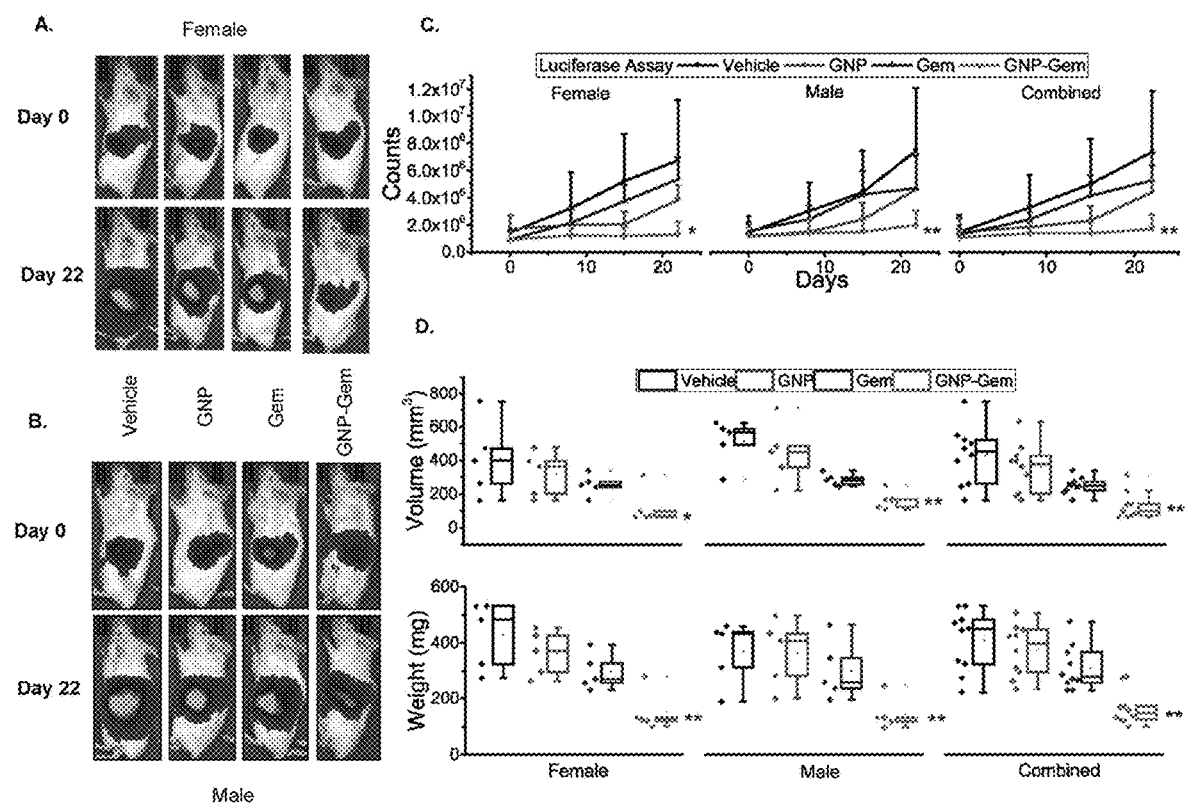
FIG. 5. In vivo therapeutic efficacy of GNP-Gem. Representative in vivo bioluminescence images captured before start and after completion of treatment for each treatment group in (A) female and (B) male mice. C. In vivo bioluminescence plot against time for female and male separately or in combination. Only (+) error bar was provided to improve clarity. * and ** denote $p<0.05$ and $p<0.01$ compared to vehicle-treated group, respectively. D. Box plot diagram depicting tumor volume and tumor weight for each treatment group in female and male separately or in combination after completion of the experiment. For comparison, individual data points from each treatment group are also provided side by side. Black=vehicle, Red=GNP, Blue=Gem, and Purple=GNP-Gem. * and ** denote $p<0.05$ and $p<0.01$ compared to vehicle-treated group, respectively.

About, $1 \times 10^6$ luciferase transfected PANC-1 cells were orthotopically implanted in the pancreas of 6-8 weeks old NSG mice. After three weeks, mice were imaged noninvasively using the Xenogen instrument to confirm tumor growth and then randomized into four groups before the initiation of treatment. Both male and female mice were included in the experiment to delineate any differential sex-dependent therapeutic effect of GNP-Gem. The experiment was terminated after three weeks of treatment. Weekly measurement of luciferase bioluminescence revealed very little tumor growth in mice receiving GNP-Gem (FIG. 5A-C). FIGS. 5A and 5B demonstrated representative bioluminescent images from each treatment group (Day 0 and Day 22 in upper and lower panels, respectively) in female and male mice, respectively. FIG. 5C depicts the tumor growth curve as measured by luciferase bioluminescence for female and male mice separately or in combination.

These results were further validated by measuring the tumor volume (FIG. 5D, upper panel) and weight (FIG. 5D, lower panel) after sacrificing the mice at the end of the experiment. The tumor volumes in GNP-Gem treated female mice (mean 123.7 mm$^3$; median 72 mm$^3$; 25th-75th percentile 67.2, 98.6) were significantly smaller compared to vehicle-treated (mean 410.5 mm$^3$; median 400.7 mm$^3$; 25th-75th percentile 262.4, 471.6; p=0.0336), GNP-treated (mean 321.2 mm$^3$; median 364.8 mm$^3$; 25th-75th percentile 202.5, 395.3; p=0.0321) or Gem-treated female mice (mean 254.8 mm$^3$; median 254.6 mm$^3$; 25th-75th percentile 241.9, 272.9; p=0.047). Similarly, GNP-Gem treated male mice exhibited significantly smaller tumor volumes (mean 137.7 mm$^3$; median 140.1 mm$^3$; 25th-75th percentile 102.2, 140.9) compared to vehicle-treated (mean 450.5 mm$^3$; median 500.2 mm$^3$; 25th-75th percentile 434.6, 520.2; p=0.0007), GNP-treated (mean 392.04 mm$^3$; median 396.6 mm$^3$; 25th-75th percentile 314.6, 425.5; p=0.0099) or Gem-treated male mice (mean 247.17 mm$^3$; median 245.3 mm$^3$; 25th-75th percentile 223.6, 259.3; p=0.0038). Combined, GNP-Gem treatment caused a significant regression in tumor volume (mean 130.75 mm$^3$; median 100.4 mm$^3$; 25th-75th percentile 72, 140) compared to vehicle (mean 430.5 mm$^3$; median 453.14 mm$^3$; 25th-75th percentile 262.4, 520.2; p=0.000094), GNP (mean 356.6 mm$^3$; median 380.09 mm$^3$; 25th-75th percentile 202.5, 425.5; p=0.00039) or Gem (mean 251 mm$^3$; median 250 mm$^3$; 25th-75th percentile 223.6, 272.9; p=0.00069). Likewise, GNP-Gem treated female mice exhibited significantly lower tumor weights (mean 152.4 mg; median 126.1 mg; 25th-75th percentile 120.1, 133.5) compared to vehicle-treated (mean 429.9 mg; median 483.8 mg; 25th-75th percentile 326.4, 531.7; p=0.0023), GNP-treated (mean 363.24 mg; median 373.1 mg; 25th-75th percentile 297.6, 426.5; p=0.0025) or Gem-treated female mice (mean 295.9 mg; median 272.4 mg; 25th-75th percentile 256.5, 326.9; p=0.0038). The tumor weights in GNP-Gem treated male mice (mean 183 mg; median 170.1 mg; 25th-75th percentile 156.4, 171.8) were significantly smaller compared to vehicle-treated (mean 385.8 mg; median 446.4 mg; 25th-75th percentile 336.8, 451.6; p=0.0049), GNP-treated (mean 384.9 mg; median 424.5 mg; 25th-75th percentile 310.7, 448.2; p=0.0061) or Gem-treated male mice (mean 325.8 mg; median 288.3 mg; 25th-75th percentile 267.5, 367.7; p=0.0208). Combined, GNP-Gem treatment caused a significant regression in tumor weight (mean 167.7 mg; median 148.35 mg; 25th-75th percentile 126.1, 171.9) compared to vehicle (mean 407.86 mg; median 449.1 mg; 25th-75th percentile 326.4, 483.6; p=0.00001), GNP (mean 374.09 mg; median 396.8 mg; 25th-75th percentile 297.6, 448.2; p=0.000014) or Gem (mean 310.86 mg; median 280.35 mg; 25th-75th percentile 126.1, 171.9; p=0.00029). No significant difference was found between GNP-Gem treated female and male mice, suggesting that the therapeutic efficacy of GNP-Gem was not sex-dependent.

Figure 6:
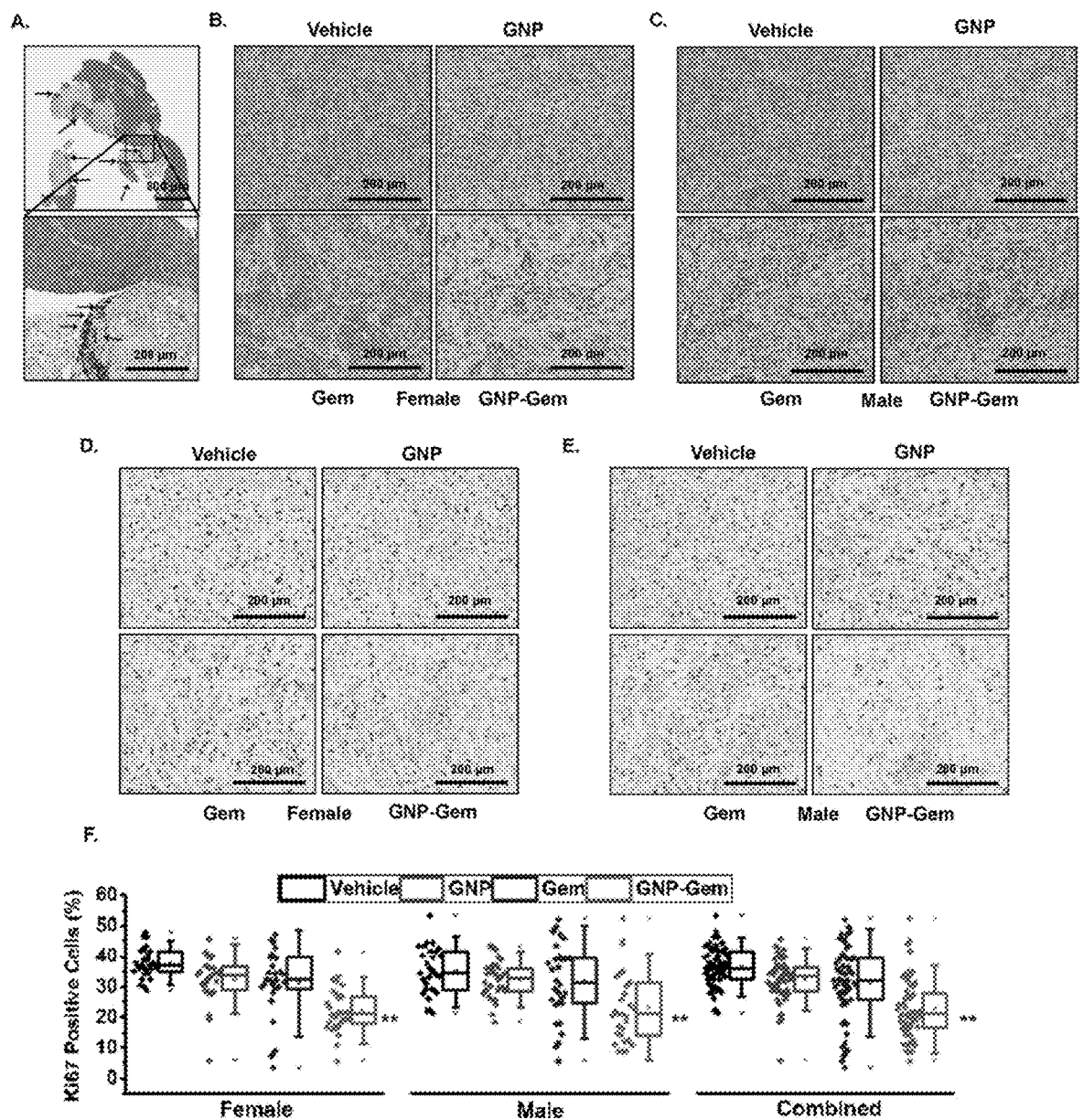
FIG. 6. Immunohistochemical analysis. A. Upper Panel, H&E staining of a tissue section from GNP-Gem treated group showing tumor-specific uptake of GNP-Gem without touching adjacent normal pancreas tissue. Scale bar=800 μm. Lower Panel, Higher magnification showing accumulation of GNPs in tumor tissue. Scale Bar=200 μm. Accumulated GNPs are shown using black arrows. B. & C. H&E staining of tissue sections obtained from each treatment group showing decrease in cellularity in GNP-Gem treated group in female and male mice respectively. Scale Bar=200 µm. D. & E. Ki67 staining of tissue sections obtained from each treatment group showing reduction in number of Ki67 positive nuclei in GNP-Gem treated group in female and male mice respectively. Scale bar=200 µm. F. Box plot diagram depicting percentage of Ki67 positive nuclei for each treatment group in female and male separately or in combination. Three slides were stained for Ki67 per treatment group and ten random areas of equal dimensions from each tissue sections were analyzed in Aperio Imagescope. For comparison, individual data points from each treatment group are also provided side by side. Black=vehicle, Red=GNP, Blue=Gem, and Purple=GNP-Gem. * and ** denote p<0.05 and p<0.01 compared to vehicle-treated group, respectively.

Accumulation of GNPs could be seen in the tumor tissues, but not in the adjacent normal pancreas tissues (FIG. 6A). This validated tumor-targeting efficacy of the synthesized GNPs for efficient delivery of Gem into the tumors. The hematoxylin and eosin staining of the formalin-fixed paraffin embedded tumor tissue sections revealed a significant loss of cellularity in Gem-conjugated GNP treatment group (FIG. 6B-C), which highlighted the in vivo antiproliferative efficacy of GNP-Gem compared to Gem or GNP alone. This was further confirmed by ki67 staining of the said tumors tissues (FIG. 6D-F). The tissues from gemcitabine-conjugated GNP-treated group exhibited the least amount of Ki67-positive nuclei. FIG. 6F depicts the quantitation of Ki67-positive nuclei in female and male mice separately or in combination. The percentage of Ki67-positive nuclei in GNP-Gem treated female mice (mean 22.2%; median 21.3%; 25th-75th percentile 17.9, 26.7) was significantly lower compared to vehicle-treated (mean 37.7%; median 37.1%; 25th-75th percentile 34.8, 41.8; p=9.81×10-14), GNP-treated (mean 32.5%; median 33.9%; 25th-75th percentile 28.8, 36.6; p=1.48×10-6) or Gem-treated female mice (mean 31.3%; median 32.3%; 25th-75th percentile 29.3, 39.5; p=0.0005). Similarly, GNP-Gem treated male mice exhibited significantly lower Ki67-positive nuclei (mean 23.3%; median 20.9%; 25th-75th percentile 14.3, 31.35) compared to vehicle-treated (mean 35.09%; median 34.3%; 25th-75th percentile 29.09, 41.35; p=1.95×10-5), GNP-treated (mean 32.3%; median 32.6%; 25th-75th percentile 28.36, 36.05; p=0.00037) or Gem-treated male mice (mean 31.5%; median 31.4%; 25th-75th percentile 24.6, 39.4; p=0.01). Combined, GNP-Gem treatment caused a significant regression in Ki67-positive nuclei (mean 22.7%; median 21.09%; 25th-75th percentile 16.6, 28) compared to vehicle (mean 36.4%; median 36.06%; 25th-75th percentile 32.5, 41.5; p=2.52×10-15), GNP (mean 32.4%; median 33.4%; 25th-75th percentile 28.7, 36.4; p=4.11×10-9) or Gem (mean 31.4%; median 32.07%; 25th-75th percentile 25.7, 39.5; p=2.41×10-5). Taken together, these results demonstrated in vivo therapeutic efficacy of GNP-Gem in a PDAC xenograft model.

In summary, the results provided herein demonstrate the successful use of an in situ reduction-based approach to synthesize highly monodispersed, spherical GNPs with a uniform size-distribution and extended stability that are surface modified with plectin-1-targeted polypeptides (e.g., polypeptides having SEQ ID NO:1 or SEQ ID NO:2). These GNPs demonstrated a remarkable efficiency in accumulating into the tumor tissue where plectin-1 is known to have an aberrant cell-surface expression, without evading into adjacent normal pancreas tissue. In addition, these GNPs displayed excellent anti-proliferative effect in established PDAC cell lines and antitumor effect in a PDAC xenograft by delivering gemcitabine selectively into the cancer cells. The results provided herein also demonstrate that the gold nanoparticles provided herein can be used to target delivery of drugs (e.g., gemcitabine) to pancreatic cancer cells (e.g., PDAC). This simple, but elegant method can be used to fabricate GNPs with suitable polypeptides that can target cell-surface receptors or proteins overexpressed in other cancers.

Example 2—Treating Pancreatic Cancer

A spontaneous pancreatic cancer model (KPC) was developed in immunocompetent C57BL/6 mouse model. After initiation of tumor, mice were divided in four groups and treated for three weeks: (1) untreated, (2) GNP (dosed at equivalent amount of gold nanoparticles to GNP-Gem), (3) Gem (2 mg/kg/day), and (4) GNP-Gem (dosed at an equivalent Gem amount of 2 mg Gem/kg/day). Mice were then sacrificed, and tumor volumes were measured. In addition, tissue samples were collected from each treatment group, and computed tomography imaging was performed.

Figure 9:
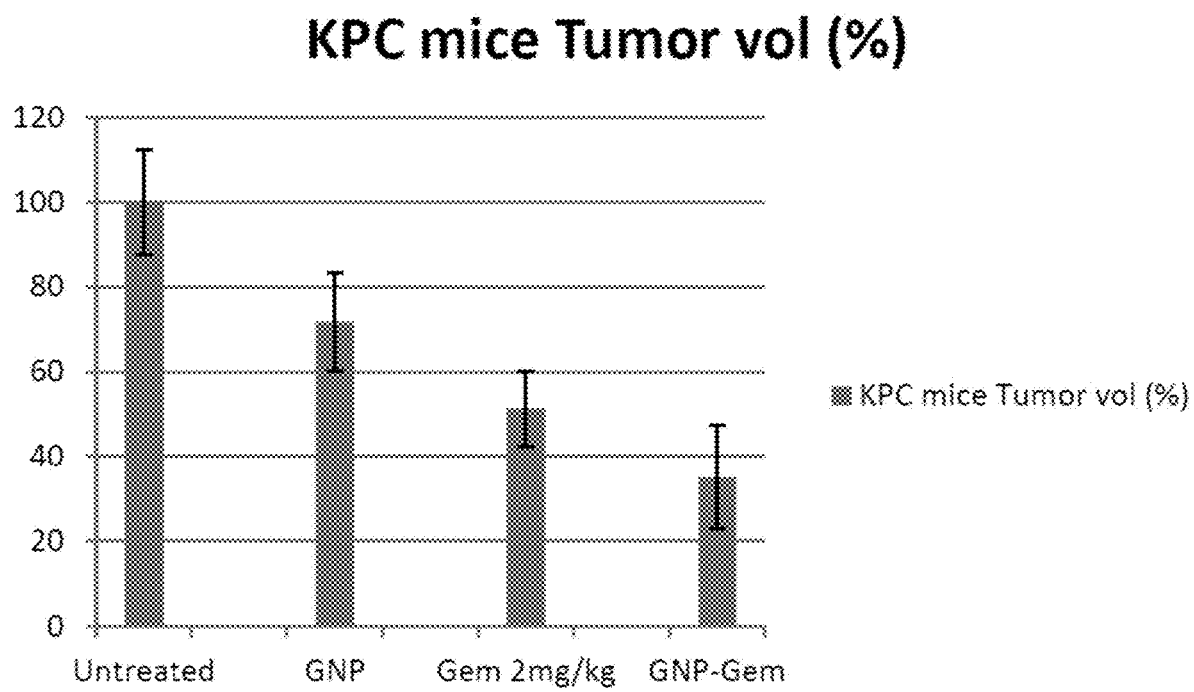
FIG. 9 is a graph plotting tumor volume as a percentage of that observed in untreated mice. These results show the in vivo therapeutic efficacy of GNP and GNP-Gem.
Figure 10:
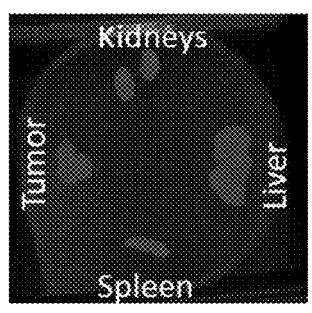
FIG. 10 contains images demonstrating the use of GNP as CT imaging contrast agent and the in vivo biodistribution GNP.
Figure 10:
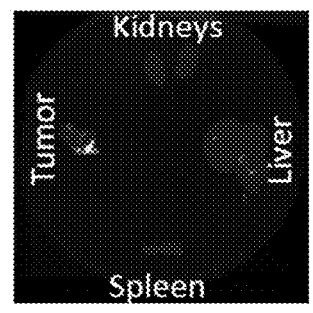
Figure 10:
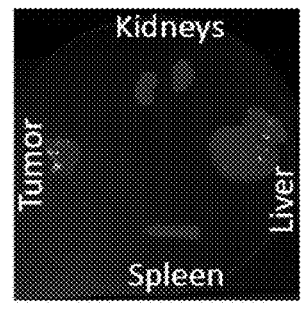

Mice treated with GNP-Gem exhibited a substantial reduction in tumor volume (FIG. 9), and computed tomography imaging displayed GNP and GNP-Gem targeted biodistribution, showing the presence of more gold nanoparticles in tumor than other organs (FIG. 10).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising gold nanoparticles having a longest dimension of from about 5 nm to about 15 nm, wherein said gold nanoparticles comprise a polypeptide comprising the amino acid sequence set forth in SEQ ID NO:2 or SEQ ID NO:1.

2. The composition of claim 1, wherein said longest dimension is from about 6 nm to about 14 nm.

3. The composition of claim 1, wherein said polypeptide comprises the amino acid sequence set forth in SEQ ID NO:2.

4. The composition of claim 1, wherein said polypeptide comprises the amino acid sequence set forth in SEQ ID NO:1.

5. A method for treating a mammal having cancer, wherein said method comprises administering, to said mammal, a composition comprising gold nanoparticles having a longest dimension of from about 5 nm to about 15 nm, wherein said gold nanoparticles comprise a polypeptide comprising the amino acid sequence set forth in SEQ ID NO:2 or SEQ ID NO:1.

6. The method of claim 5, wherein said mammal is a human.

7. The method of claim 5, wherein said cancer is pancreatic cancer, liver cancer, lung cancer, breast cancer, hepatocellular carcinoma, prostate cancer, neuroblastoma, or cholangiocarcinoma.

8. A method for treating a mammal having pancreatic cancer, wherein said method comprises administering, to said mammal, a composition comprising gold nanoparticles having a longest dimension of from about 5 nm to about 15 nm, wherein said gold nanoparticles comprise a polypeptide comprising the amino acid sequence set forth in SEQ ID NO:2 or SEQ ID NO:1, and wherein said gold nanoparticles enter cancer cells present within said mammal without entering more than 10 percent of non-cancerous pancreatic cells of said mammal.

9. The method of claim 8, wherein said mammal is a human.

10. The method of claim 8, wherein said gold nanoparticles enter less than 5 percent of said non-cancerous pancreatic cells.

* * * * *